US007135282B1

(12) United States Patent
Hellendoorn et al.

(10) Patent No.: US 7,135,282 B1
(45) Date of Patent: Nov. 14, 2006

(54) VIRAL PARTICLES WITH EXOGENOUS INTERNAL EPITOPES

(75) Inventors: Koen Hellendoorn, Newmarket (GB); Tim Jones, Babraham Cambridge (GB)

(73) Assignee: The Dow Chemical Company, Midland, MI (US)

( * ) Notice: Subject to any disclaimer, the term of this patent is extended or adjusted under 35 U.S.C. 154(b) by 746 days.

(21) Appl. No.: 10/110,511

(22) PCT Filed: Oct. 13, 2000

(86) PCT No.: PCT/US00/28430

§ 371 (c)(1),
(2), (4) Date: Apr. 12, 2002

(87) PCT Pub. No.: WO01/27282

PCT Pub. Date: Apr. 19, 2001

(30) Foreign Application Priority Data

Oct. 14, 1999  (GB)  ................................. 9924352.9

(51) Int. Cl.
*C12N 7/00*  (2006.01)
*A61K 36/00*  (2006.01)
(52) U.S. Cl. ..................... 435/5; 435/235.1; 435/235.6; 435/320.1; 530/806; 530/826; 424/184.1
(58) Field of Classification Search ............. 435/235.1, 435/235.6, 320.1; 530/826, 806; 424/184.1
See application file for complete search history.

(56) References Cited

U.S. PATENT DOCUMENTS

| | | | |
|---|---|---|---|
| 4,677,066 A | 6/1987 | Takahashi et al. | 435/172.2 |
| 4,743,548 A | 5/1988 | Crossway et al. | 435/172.3 |
| 5,149,645 A | 9/1992 | Hoekema et al. | 435/172.3 |
| 5,352,605 A | 10/1994 | Fraley et al. | 435/240.4 |
| 5,508,184 A | 4/1996 | Negrutiu et al. | 435/172.3 |
| 5,584,807 A | 12/1996 | McCabe | 604/71 |
| 5,589,367 A | 12/1996 | Donson et al. | 435/172.3 |
| 5,874,087 A | 2/1999 | Lomonossoff et al. | 424/199.1 |
| 5,958,422 A | 9/1999 | Lomonossoff | 424/199.1 |
| 6,110,466 A * | 8/2000 | Lomonossoff et al. | 424/199.1 |

FOREIGN PATENT DOCUMENTS

| WO | WO 95/14098 | 5/1995 |
|---|---|---|
| WO | WO 98/56933 | 12/1998 |

OTHER PUBLICATIONS

Brennan FR. et al. *Pseudomonas aeruginosa* outer-membrane protein F epitopes are highly immunogenic in mice when expressed on a plant virus. Microbiology (1999) 145, 221-220.*
Bendahmane et al., "Display of Epitopes on the SUrface of Tobacco Mosaic Virus: Impact of Charge and Isoelectric Point of the Epitope on Virus-Host Interactions" *J. Mol. Biol.* 290(1):9-20 (1999).
Brennan et al., "*Pseudomonas aeruginosa* outer-membrane protein F epitopes are highly immunogenic in mice when expressed on a plany virus" *Microbiology* 145: 211-220 1999.
Daisgaard et al., "Plant-derived vaccine protects target animals against a viral disease" *Nature Biotechnology* 15: 248-252 (1997).
Del Val et al., Efficient Processing of an Antigenic Sequence for Presentation by MHC Class I Molecules Depends on Its Neighboring Residues in the Protein: *Cell* 66: 1145-1153 (1991).
Dessens & Lomonossoff, "Cauliflower mosaic virus 35S promoter-controlled DNA copies of cowpea mosaic virus RNAs are infectious on plants" *Journal of General Virology* 74: 889-892 (1993).
Evans et al., *Handbook of Plant Cell Culture*, 1: 124-176, MacMillan Publishing Co., New York (1983).
Garbarino and Belknap, "Isolation of a ubiquitin-ribosomal protein gene (ubi3l ) from potato and expression of its promoter in transgenic plants" *Plant Molecular Biology* 24: 119-127 (1994).
Goldbach et al., "Independent replication and expression of B-component RNA of cowpea mosaic virus" *Nature* 286: 297-300 (1980).
Layton et al., "Induction of single and dual cytotoxic T-lymphocyte responses to viral proteins in mice using recombinant hybrid Ty-virus-like particles" *Immunology* 87: 171-178 (1996).
Lin et al., "Structural Fingerprinting: Subgrouping of Comoviruses by Structural Studies of Red Clover Mottle Virus to 2.4-A Resolution and Comparisons with Other Comoviruses" *Journal of Virology* 74(1): 493-504 (1999).
Lomonossoff and Shanks, "The nucleotide sequence of cowpea mosaic virus B RNA" *The EMBO Journal* 2: 2253-2258 (1983).
Maniatis et al., "Regulation of Inducible and Tissue-Specific Gene Expression" *Science* 236: 1237-1244 (1987).
Potrykus and Shillito, "Protoplasts: Isolation, Culture, Plant Regeneration" *Methods in Enzymology*, 118: 549-578 (1986).
Sambrook, et al., "Splicing Signals" *A Molecular Cloning: A Laboratory Manual*, 2nd ed., Cold Spring Harbor Laboratory Press, New York 16.7-16.8 (1989).
van Kammen and de Jaeger, Cowpea Mosaic Virus, In: CMI/AAB Description of Plant Viruses 197, Commonwealth Agricultural Bureax [1978 ].
van Wezenbeek et al., "Primary structure and gene organization of the middle-component RNA of cowpea mosaic virus" *The EMBO Journal* 2: 941-946 (1983).

(Continued)

*Primary Examiner*—Jeffrey Stucker
*Assistant Examiner*—Bo Peng
(74) *Attorney, Agent, or Firm*—Jarett Abramson

(57) ABSTRACT

The present invention relates to the expression of peptides on viral particles, and more particularly to the expression of peptides on the interior or the viral capsid. Methods are described for modifying viruses so that exogenous epitopes are expressed on the interior of the viral capsid. Viruses that can be modified include (+) stranded RNA viruses, especially plant (+) stranded RNA viruses such as the cowpea mosaic virus. Internal expression is especially useful for the expression of hydrophobic epitopes. The modified viral particles also find use as vaccines and as such are capable of eliciting an immune response.

10 Claims, 3 Drawing Sheets

OTHER PUBLICATIONS

Figure 2:
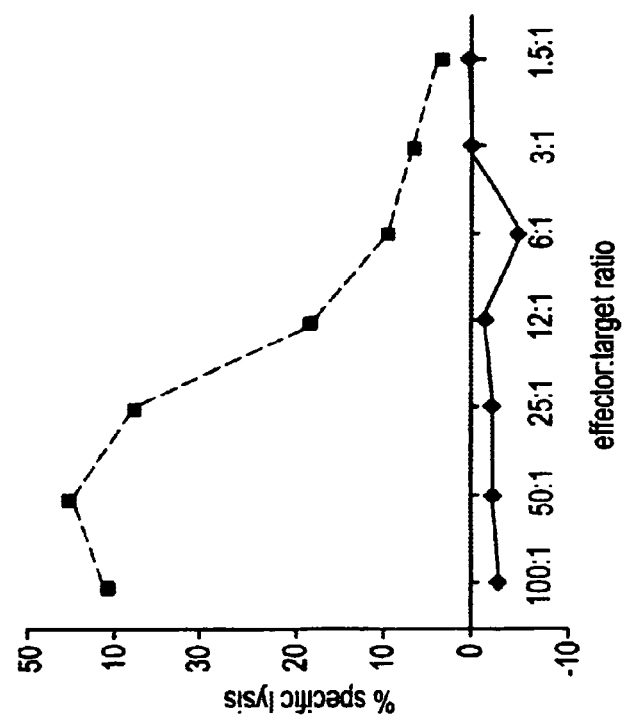
Figure 3:
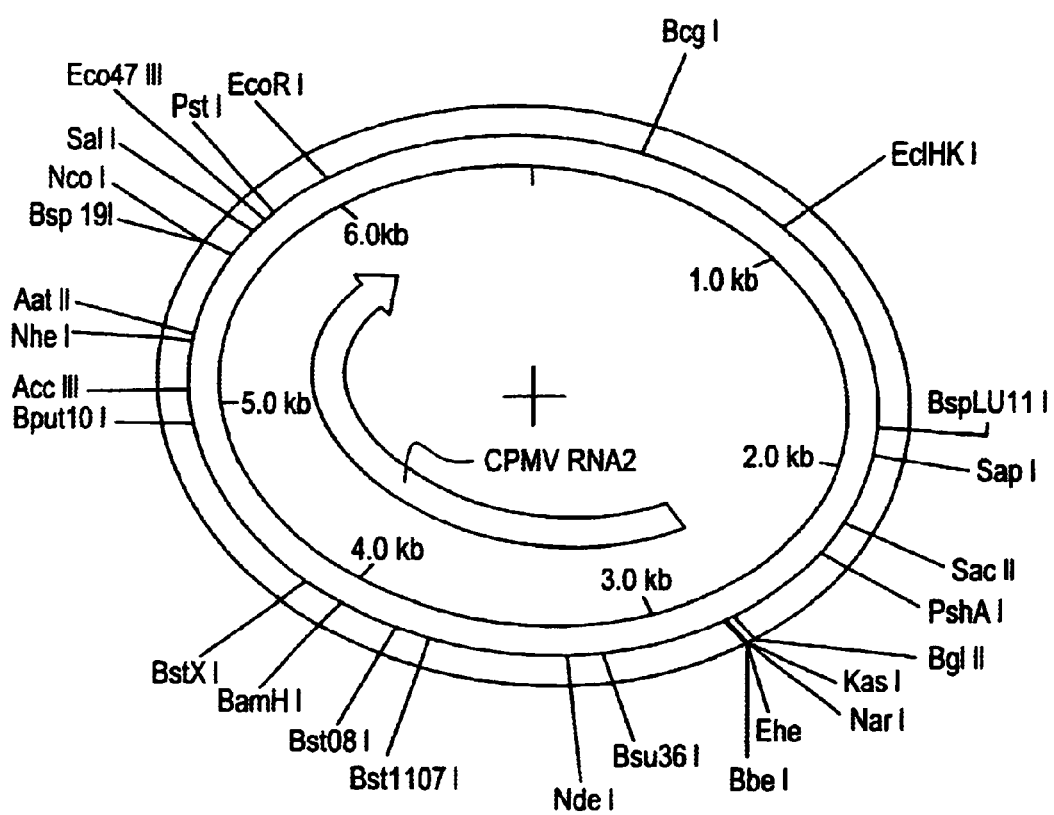

Verver et al., "Studies on the Movement of Cowpea Mosaic Virus Using the Jellyfish Green Fluorescent Protein" *Virology* 242: 22-27 (1998).

Voss et al., "The role of enhancers in the regulation of cell-type-specific transcriptional control" *Trends Biochem. Sci.,* 11: 287-289 (1986).

* cited by examiner

FIG. 1

Insertions in the N-terminus of CPMV VP-S pCP26:
CAAGGACCTGTTTGTGCTGAAGCCTCAGATGTGTATAGCCCATGTATGATAGCTAGCACTCCTCCTGC
GTTCCTGGACAAACACGACTTCGGAGTCTACACATATCGGGTACATACTATCGATCGTGAGGAGGACG
 Q  G  P  V  C  A  E  A  S  D  V  Y  S  P  C  M  I  A  S  T  P  P  A With NheI/Eco0109I:
CAAG                    CTAGCACTCCTCCTGC
GTTCCTG                          GTGAGGAGGACG Inserts:
GACCTGTTTGTGCTGAAGCCTCAGATGTGTAT    -epitope-    TATAGCCCATGTATGATAG
GACAAACACGACTTCGGAGTCTACACATA                    ATATCGGGTACATACTATCGATC
                                                         ↑
                                                   duplication
                                                     of y$_{11}$

SEQUENCE LISTING

<160> NUMBER OF SEQ ID NOS: 37

<210> SEQ ID NO 1

```
<211> LENGTH: 10
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 1

Gly Pro Val Cys Ala Glu Ala Ser Asp Val
1               5                   10

<210> SEQ ID NO 2
<211> LENGTH: 11
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 2

Gly Pro Val Cys Ala Glu Ala Ser Asp Val Tyr
1               5                   10

<210> SEQ ID NO 3
<211> LENGTH: 9
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 3

Gly Pro Val Cys Ala Glu Ala Ser Asp
1               5

<210> SEQ ID NO 4
<211> LENGTH: 7
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 4

Gly Tyr His Gly Ser Ser Leu
1               5

<210> SEQ ID NO 5
<211> LENGTH: 14
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 5

Ala Val Tyr Tyr Cys Thr Arg Gly Tyr His Gly Ser Ser Leu
1               5                   10

<210> SEQ ID NO 6
<211> LENGTH: 15
<212> TYPE: PRT
<213> ORGANISM: Artificial Sequence
<220> FEATURE:
```

```
<221> NAME/KEY: misc_feature
<222> LOCATION: ()..()
<223> OTHER INFORMATION: Synthetic

<400> SEQUENCE: 6

Arg Pro Gln Ala Ser Gly Val Tyr Met Gly Asn Leu Thr Ala Gln
1               5                   10                  15

<210> SEQ ID NO 7
<211> LENGTH: 9
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 7

Ser Tyr Ile Pro Ser Ala Glu Lys Ile
1               5

<210> SEQ ID NO 8
<211> LENGTH: 9
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 8

Ser Tyr Ile Pro Ser Ala Gly Lys Ile
1               5

<210> SEQ ID NO 9
<211> LENGTH: 16
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 9

Ala Ala Ala Ser Tyr Ile Pro Ser Ala Glu Lys Ile Ala Ala Ala Ala
1               5                   10                  15

<210> SEQ ID NO 10
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 10

Ala Pro Gly Asn Tyr Pro Ala Leu
1               5

<210> SEQ ID NO 11
<211> LENGTH: 16
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic
```

```
<400> SEQUENCE: 11

His Gly Glu Phe Ala Pro Gly Asn Tyr Pro Ala Leu Trp Ser Tyr Ala
1               5                   10                  15

<210> SEQ ID NO 12
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 12

Arg Gly Tyr Val Tyr Gln Gly Leu
1               5

<210> SEQ ID NO 13
<211> LENGTH: 9
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 13

Leu Asp Arg Leu Val Arg Leu Ile Gly
1               5

<210> SEQ ID NO 14
<211> LENGTH: 15
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 14

Ala Ala Ala Leu Asp Arg Leu Val Arg Leu Ile Gly Ala Ala Ala
1               5                   10                  15

<210> SEQ ID NO 15
<211> LENGTH: 18
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 15

Val Asp Asp Ala Leu Ile Asn Ser Thr Lys Ile Tyr Ser Tyr Phe Pro
1               5                   10                  15

Ser Val

<210> SEQ ID NO 16
<211> LENGTH: 13
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 16
```

```
Met Gln Trp Asn Ser Thr Thr Phe His Gln Thr Leu Gln
1               5                   10
```

<210> SEQ ID NO 17
<211> LENGTH: 5
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 17

```
Ala Ala Ala Ala Ala
1               5
```

<210> SEQ ID NO 18
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 18
ggttatcatg gttctagttt g                                             21

<210> SEQ ID NO 19
<211> LENGTH: 42
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 19
gctgtttatt attgtactag aggttatcat ggttctagtt tg                      42

<210> SEQ ID NO 20
<211> LENGTH: 45
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 20
agacctcaag cttctggtgt ttatatgggt aatttgactg ctcaa                   45

<210> SEQ ID NO 21
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 21
tcttatattc cttctgctga aaagatt                                       27

<210> SEQ ID NO 22
<211> LENGTH: 48
<212> TYPE: DNA
<213> ORGANISM: Artificial Sequence

```
<220> FEATURE:
<221> NAME/KEY: misc_feature
<222> LOCATION: ()..()
<223> OTHER INFORMATION: Synthetic

<400> SEQUENCE: 22
gcagcggcct cttatattcc ttctgctgaa aagattgcgg ccgctgct                    48

<210> SEQ ID NO 23
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 23
gctcctggta attatcctgc tttg                                              24

<210> SEQ ID NO 24
<211> LENGTH: 48
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 24
catggtgaat tgctcctgg taattatcct gctttgtggt cttatgct                     48

<210> SEQ ID NO 25
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 25
agaggttatg tttatcaagg ttg                                               23

<210> SEQ ID NO 26
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 26
ttggatagat tggttagatt gattggt                                           27

<210> SEQ ID NO 27
<211> LENGTH: 45
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 27
gcagcggcct tggatagatt ggttagattg attggggccg ctgct                       45
```

<210> SEQ ID NO 28
<211> LENGTH: 54
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 28
gtggatgatg ctttgattaa ttctactaag atttatagtt attttccttc tgtt        54

<210> SEQ ID NO 29
<211> LENGTH: 39
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 29
atgcaatgga actctactac ttttcatcaa actttgcaa                         39

<210> SEQ ID NO 30
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 30
gcagcggccg ctgct                                                   15

<210> SEQ ID NO 31
<211> LENGTH: 9
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 31

Tyr Ser Pro Cys Met Ile Ala Ser Thr
1               5

<210> SEQ ID NO 32
<211> LENGTH: 10
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 32

Val Tyr Ser Pro Cys Met Ile Ala Ser Thr
1               5                   10

<210> SEQ ID NO 33
<211> LENGTH: 15
<212> TYPE: PRT
<213> ORGANISM: Artificial Sequence
<220> FEATURE:
<221> NAME/KEY: misc_feature

```
<222> LOCATION: ()..()
<223> OTHER INFORMATION: Synthetic

<400> SEQUENCE: 33

Ala Val Tyr Tyr Cys Thr Arg Gly Tyr His Gly Ser Ser Leu Tyr
1               5                   10                  15

<210> SEQ ID NO 34
<211> LENGTH: 8
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 34

Gly Tyr His Gly Ser Ser Leu Tyr
1               5

<210> SEQ ID NO 35
<211> LENGTH: 16
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 35

Gly Val Ser Thr Ala Pro Asp Thr Arg Pro Ala Pro Gly Ser Thr Ala
1               5                   10                  15

<210> SEQ ID NO 36
<211> LENGTH: 32
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 36

Thr Asp Ala Tyr Asn Gln Lys Leu Ser Glu Arg Arg Ala Gly Ala Asp
1               5                   10                  15

Asn Ala Thr Ala Glu Gly Arg Ala Ile Asn Arg Arg Val Glu Ala Glu
                20                  25                  30

<210> SEQ ID NO 37
<211> LENGTH: 16
<212> TYPE: PRT
<213> ORGANISM: Artificial Sequence
<220> FEATURE:
<221> NAME/KEY: misc_feature
<222> LOCATION: ()..()
<223> OTHER INFORMATION: Synthetic

<400> SEQUENCE: 37

Gly Val Thr Ser Ala Pro Asp Thr Arg Pro Ala Pro Gly Ser Thr Ala
1               5                   10                  15
```

VIRAL PARTICLES WITH EXOGENOUS INTERNAL EPITOPES

CROSS-REFERENCE TO RELATED APPLICATION

This application claims priority from Great Britain application 9924352.9, filed Oct. 14, 1999, now abandoned.

FIELD OF THE INVENTION

The present invention relates to the expression of peptides on viral particles, and more particularly to the expression of peptides on the interior of the viral capsid.

BACKGROUND

Vaccines are one of the greatest achievements of biomedical science and public health. At the beginning of the 20th century, infectious diseases were widely prevalent in the United States and exacted an enormous toll on the population. For example, in 1900, 21,064 smallpox cases were reported, and 894 patients died. In 1920, 469,924 measles cases were reported, and 7575 patients died; 147,991 diphtheria cases were reported, and 13,170 patients died. In 1922, 107,473 pertussis cases were reported, and 5099 patients died. These diseases have largely been eliminated in the United States.

Despite this success, more than 5 million infants worldwide die every year from diseases that could be avoided with existing vaccines. However, many of the current vaccines must be refrigerated which makes their distribution in developing countries difficult. Furthermore, vaccines are either nonexistent or not available for diseases associated with significant rates of morbidity or mortality. For example, more than 250 million people are chronically infected with hepatitis B virus, malaria causes 1–2 million deaths each year; diarrheal diseases (for example, infections caused by rotovirus, *Shigella* sp., *Vibrio cholera*, and toxin producing *E. coli*) annually kill more an estimated 4–5 million people.

The Center for Disease Control has identified several factors for achieving the full potential of vaccines (www.cdc.gov/epo/mmwr/preview/mmwrhtml/00056803.htm). These suggestions include pursuing new approaches to vaccine delivery and administration. One new approach is the development of vaccines that stimulate the two types of immune responses: humoral responses mediated by B cells and cellular responses mediated by helper T-cells.

However, attempts to create vaccines that stimulate both humoral and cellular immune responses or preferentially induce a cellular immune response have met with difficulty. For example, synthetic peptide vaccines and recombinant protein vaccines are often poorly immunogenic and tend to induce humoral responses and not to induce cellular immune responses. DNA vaccines can induce both humoral and cellular immune responses. However, questions remain as to what the consequences of long-term antigen expression will be.

Accordingly, what is needed in the art are improved delivery mechanisms for vaccines. In particular, the delivery mechanism should be useful inducing both cellular and humoral immune responses.

SUMMARY OF THE INVENTION

The present invention relates to the expression of peptides on viral particles, and more particularly to the expression of peptides on the interior or the viral capsid. In some embodiments, the present invention provides a compound comprising a chimeric viral particle having a capsid, wherein the capsid has an interior side and an exterior side, the capsid comprising at least one exogenous peptide on said interior side of the capsid. In some preferred embodiments, the viral particle is capable of assembly in a host cell or tissue. In some embodiments, the viral particle is icosahedral. In some preferred embodiments, the viral particle is a comovirus. In some particularly preferred embodiments, the viral particle is cowpea mosaic virus. In some embodiments, the exogenous peptide is inserted in a coat protein of the viral particle. In some preferred embodiments, the exogenous peptide has 5 to 20 amino acids. In other preferred embodiments, the exogenous peptide is inserted at a point from 5 to 20 amino acids from the N-terminus of a coat protein such assembly of the viral particle is not precluded in a host cell. In some particularly preferred embodiments, the exogenous peptide is inserted in VP-S of cowpea mosaic virus between a tyrosine residue at position 11 and a duplicated tyrosine residue at position 12. In other particularly preferred embodiments, the exogenous peptide is inserted in VP-S of cowpea mosaic virus between a dipeptide comprising a valine residue at position 10 and a tyrosine residue at position 11 and a duplicated dipeptide comprising a valine residue at position 12 and a tyrosine residue at position 13. In still other preferred embodiments, the exogenous peptide is inserted in VP-S of cowpea mosaic virus between a valine residue at position 10 and a duplicated valine residue at position 11. In further embodiments, the viral particle does not contain nucleic acid.

In other embodiments, the exogenous peptide encodes an epitope recognizable by an animal immune system. In some preferred embodiments, the exogenous epitope is a cytotoxic T lymphocyte epitope. In particularly preferred embodiments, the exogenous peptide contains a cytotoxic T lymphocyte epitope with flanking amino acids derived from a naturally occurring source of the epitope. In some embodiments, the exogenous peptide is a T helper cell epitope. In some preferred embodiments, the exogenous peptide contains a T helper cell epitope with flanking amino acid sequences derived from a naturally occurring source of the epitope. In still other embodiments, the exogenous peptide is a B cell epitope. In further embodiments, the exogenous peptide contains a T helper cell epitope with flanking amino acid sequences derived from a naturally occurring source of the epitope.

In some embodiments, the chimeric viral particle contains a second exogenous peptide expressed on the outer surface of the viral capsid. In preferred embodiments, the second exogenous peptide is expressed on the outer surface of the viral capsid, wherein said peptide is inserted in the βC'-βC" loop of VP-S of cowpea mosaic virus. In other preferred embodiments the second exogenous peptide is expressed on the outer surface of the viral capsid, wherein said peptide is inserted in the βB-βC loop of VP-S of cowpea mosaic virus. In still other preferred embodiments the second exogenous peptide is expressed on the outer surface of the viral capsid, wherein said peptide is inserted in the βE-αB loop of VP-L of cowpea mosaic virus.

In other embodiments, the present invention provides a vaccine composition characterized in having an effective amount of a viral particle comprising a capsid having an interior side and an exterior side, said capsid comprising at least one exogenous peptide, wherein said exogenous peptide is on said interior side of said capsid. In still other embodiments the present invention provides a formulation which comprises as an active ingredient a viral particle comprising a capsid having an interior side and an exterior side, said capsid comprising at least one exogenous peptide, wherein said exogenous peptide is on said interior side of said capsid and an adjuvant.

In some embodiments, the present invention provides a compound comprising a viral coat protein, wherein said viral coat protein includes an exogenous peptide, said viral coat protein is configured so as to assemble into a viral capsid having an interior side and an exterior side, wherein said exogenous peptide is expressed on said interior side of said viral capsid.

In further embodiments, the present invention provides a process for preparing a viral particle comprising providing a host cell and nucleic acid encoding a viral particle, said viral particle comprising i) a viral coat protein, said viral coat protein comprising an interior side and an exterior side, and ii) an exogenous peptide, wherein said exogenous peptide is inserted on said interior side of said viral coat protein; transfecting said host cell with said nucleic acid so that viral particles are produced.

In still other embodiments, the present invention provides a method of inducing an immune response in an animal requiring such treatment which method comprises administering to an animal a viral particle comprising a capsid having an interior side and an exterior side, said capsid comprising at least one exogenous peptide, wherein said exogenous peptide is on said interior side of said capsid.

In still further embodiments, the present invention provides a product obtainable by the process comprising providing a host cell and nucleic acid encoding a viral particle, said viral particle comprising i) a viral coat protein, said viral coat protein comprising an interior side and an exterior side, and ii) an exogenous peptide, wherein said exogenous peptide is inserted on said interior side of said viral coat protein; transfecting said host cell with said nucleic acid so that viral particles are produced.

In some embodiments, the present invention provides a commercial package comprising a viral particle comprising a capsid having an interior side and an exterior side, said capsid comprising at least one exogenous peptide, wherein said exogenous peptide is on said interior side of said capsid as an active ingredient together with instructions for use thereof. In other embodiments, the present compound comprising a chimeric virus particle expressing an internal epitope as described herein in any of the examples.

In some embodiments, the present invention provides a vector comprising nucleic acid encoding a viral particle, the viral particle comprising i) a viral coat protein comprising an interior side and an exterior side, and ii) an exogenous peptide, wherein said exogenous peptide is inserted on the interior side of the viral coat protein. The present invention is not limited to any particular type of vector. Indeed, a variety of vectors are contemplated, including, but not limited to RNA vectors (for example, nucleic acid encoding a (+) stranded RNA virus) or DNA vectors (for example, plasmid DNA encoding a (+) stranded RNA virus). Likewise, the present invention is not limited to any particular viral particle. Indeed, a variety of viral particles are contemplated, including, but not limited to, rod-shaped viral particles and icosohedral-shaped viral particles. The present invention is not limited to any particular plant (+) stranded virus. Indeed, a variety of plant (+) stranded RNA viruses find use in the present invention. In some preferred embodiments, the plant (+) stranded RNA virus is a comovirus. In particularly preferred embodiments, the plant (+) stranded RNA virus is cowpea mosaic virus.

In some embodiments, the coat protein is derived from a (+) stranded RNA virus. The present invention is not limited to coat proteins from any particular (+) stranded RNA virus. Indeed, coat proteins from a variety of (+) stranded RNA viruses are contemplated. In some preferred embodiments, the coat protein is from a plant (+) stranded RNA virus. The present invention is not limited to insertion of the exogenous peptide at any particular location. Indeed, insertion at a variety of locations is contemplated. In some embodiments, the viral coat protein has an N-terminus, and the exogenous peptide is inserted at a position from 5 to 20 amino acids from the N-terminus so that assembly of said viral coat protein is not precluded. In some preferred embodiments, the viral coat protein is VP-S of cowpea mosaic virus and the exogenous peptide is inserted between a tyrosine residue at position 11 of the VP-S and a duplicated tyrosine residue engineered at position 12 of the VP-S. In other preferred embodiments, the viral coat protein is VP-S of cowpea mosaic virus and the exogenous peptide is inserted between a dipeptide comprising a valine residue at position 10 and a tyrosine residue at position 11 of the VP-S, and a duplicated dipeptide comprising a valine residue engineered at position 12 and a tyrosine residue engineered at position 13 of the VP-S.

The present invention is not limited to exogenous peptides of any particular type. Indeed, a variety of exogenous peptides can be expressed in the vectors of the present invention. In some embodiments, the exogenous peptide is hydrophobic. In other embodiments, the exogenous peptide is a cytotoxic T lymphocyte epitope. In further embodiments, the exogenous peptide is a helper T cell epitope. In still other embodiments, the exogenous peptide is a B cell epitope.

The present invention is not limited to vectors encoding only a single exogenous peptide. Indeed, the present invention contemplates that more than one exogenous peptide can be expressed from the vectors. In some embodiments, the viral coat protein further comprises a second exogenous peptide. In preferred embodiments, the second exogenous peptide is inserted on the exterior side of said viral coat protein. In some particularly preferred embodiments, the viral coat protein is VP-S having a βC'-βC" loop and the second exogenous peptide is inserted in said βC'-βC" loop. In other preferred embodiments, the viral coat protein is VP-L having a βE-αB loop and the second exogenous peptide is inserted in said βE-αB loop.

The vectors of the present invention also include other components, such as regulatory elements. In some embodiments, the nucleic acid further encodes a promoter operably linked to the nucleic acid encoding a viral particle. The present invention is not limited to any particular promoter. Indeed, a variety of promoters are contemplated, including, but not limited to tissue specific plant promoters and constitutive plant promoters.

In other embodiments, the present invention provides methods comprising providing i) the vector described above and ii) host cells; and b) transfecting the host cells with the vector to produce transfected host cells under conditions such that the transfected host cells express the viral particle. The present invention is not limited to the transfection of any particular host cells. Indeed, the transfection of a variety of host cells is contemplated, including, but not limited to, host cells selected from the group consisting of cells in planta, plant tissue culture cells, plant protoplasts, and cells in plant tissue. In still further embodiments, the present invention encompasses host cells produced by these methods.

In some embodiments, the present invention provides methods comprising providing a plant transfected with the vector described above and growing the plant under conditions such that the viral particle is produced. In some preferred embodiments, the methods further comprise the step of purifying the viral particles from the plant.

In further embodiments, the present invention provides compositions comprising a nucleic acid encoding a viral coat protein comprising an exogenous peptide, the viral coat protein is configured so as to assemble into a viral capsid having an interior side and an exterior side, wherein the exogenous peptide is expressed on the interior side of the viral capsid. The present invention is not limited to any particular type of nucleic acid. Indeed, a variety of nucleic acids are contemplated, including, but not limited to RNA (for example, nucleic acid encoding a (+) stranded RNA virus) or DNA (for example, plasmid DNA encoding a (+) stranded RNA virus). Likewise, the present invention is not limited to any particular viral particle. Indeed, a variety of viral particles are contemplated, including, but not limited to, rod-shaped viral particles and icosohedral-shaped viral particles. The present invention is not limited to any particular plant (+) stranded virus. Indeed, a variety of plant (+) stranded RNA viruses find use in the present invention. In some preferred embodiments, the plant (+) stranded RNA virus is a comovirus. In particularly preferred embodiments, the plant (+) stranded RNA virus is cowpea mosaic virus.

In some embodiments, the coat protein is derived from a (+) stranded RNA virus. The present invention is not limited to coat proteins from any particular (+) stranded RNA virus. Indeed, coat proteins from a variety of (+) stranded RNA viruses are contemplated. In some preferred embodiments, the coat protein is from a plant (+) stranded RNA virus. The present invention is not limited to insertion of the exogenous peptide at any particular location. Indeed, insertion at a variety of locations is contemplated. In some embodiments, the viral coat protein has an N-terminus, and the exogenous peptide is inserted at a position from 5 to 20 amino acids from the N-terminus so that assembly of said viral coat protein is not precluded. In some preferred embodiments, the viral coat protein is VP-S of cowpea mosaic virus and the exogenous peptide is inserted between a tyrosine residue at position 11 of the VP-S and a duplicated tyrosine residue engineered at position 12 of the VP-S. In other preferred embodiments, the viral coat protein is VP-S of cowpea mosaic virus and the exogenous peptide is inserted between a dipeptide comprising a valine residue at position 10 and a tyrosine residue at position 11 of the VP-S, and a duplicated dipeptide comprising a valine residue engineered at position 12 and a tyrosine residue engineered at position 13 of the VP-S.

The present invention is not limited to exogenous peptides of any particular type. Indeed, a variety of exogenous peptides can be expressed in the vectors of the present invention. In some embodiments, the exogenous peptide is hydrophobic. In other embodiments, the exogenous peptide is a cytotoxic T lymphocyte epitope. In further embodiments, the exogenous peptide is a helper T cell epitope. In still other embodiments, the exogenous peptide is a B cell epitope.

The present invention is not limited to nucleic acids encoding only a single exogenous peptide. Indeed, the present invention contemplates that more than one exogenous peptide can be encoded by the nucleic acids. In some embodiments, the viral coat protein further comprises a second exogenous peptide. In preferred embodiments, the second exogenous peptide is inserted on the exterior side of the viral coat protein. In some particularly preferred embodiments, the viral coat protein is VP-S having a βC'-βC" loop and the second exogenous peptide is inserted in said βC'-βC" loop. In other preferred embodiments, the viral coat protein is VP-L having a βE-αB loop and the second exogenous peptide is inserted in said βE-αB loop.

The nucleic acids of the present invention also include other components, such as regulatory elements. In some embodiments, the nucleic acids further encode a promoter operably linked to the nucleic acid encoding a viral particle. The present invention is not limited to any particular promoter. Indeed, a variety of promoters are contemplated, including, but not limited to tissue specific plant promoters and constitutive plant promoters.

In still further embodiments, the present invention provides viral particles comprising a capsid having an interior side and an exterior side, the capsid comprising at least one exogenous peptide, wherein the exogenous peptide is on the interior side of the capsid. The present invention is not limited to any particular viral particle. Indeed, as described above, the present invention encompasses a wide variety of viral particles. In some embodiments, the present invention provides a plant expressing the viral particles. In further embodiments, the present invention provides fruit, leaves, tubers, stems or purified viral particles isolated from the plant.

In other embodiments, the present invention provides methods for inducing an immune response comprising providing i) viral particles (described above) comprising a plurality of coat proteins having an interior side and an exterior side, the coat proteins comprising an exogenous peptide, wherein the exogenous peptide is on the interior side of the coat proteins; and ii) a subject; and b) exposing the subject to the viral particle under conditions such that the subject develops an immune response to the exogenous peptide. In some preferred embodiments, the viral particles are provided from a plant source.

In still further embodiments, the present invention provides vectors comprising nucleic acid encoding a viral coat protein sequence having inserted therein an exogenous peptide sequence, the viral coat protein comprising a second site mutation such that the viral coat protein is capable of being assembled into a viral capsid. The present invention not limited to any particular second site mutations. Indeed, a variety of second site mutation are contemplated, including, but not limited to, second site mutations in both the VP-S and VP-L of cow pea mosaic virus. In particularly preferred embodiments, the second site mutation is selected from the group consisting of F91S in VP-S, F180L in VP-S, M177V in VP-S, I124V in VP-S, R2102K in VP-L, I2045M in VP-L, M177T in VP-S, A2092T in VP-L, G80D in VP-S.

In some embodiments, the present invention provides methods for inducing second site mutations in a viral coat protein comprising providing i) a vector comprising nucleic acid encoding a viral particle, the viral particle comprising a viral coat protein, the viral coat protein comprising an interior side and an exterior side, and ii) a foreign peptide, wherein the foreign peptide is inserted on the interior side of the viral coat protein and ii) a first host plant; infecting the first host plant with the vector so that the viral particle is expressed; monitoring the first host plant until late lesions appear (e.g. in directly infected leaves); isolating viral particles from the late lesions to provide isolated viral particles; and inoculating a second host plant to obtain a secondary infection. In some embodiments, the methods further comprise the step of monitoring the second host plant for the appearance of systemic symptoms. In some preferred embodiments, the systemic symptoms appear in a time frame comparable to that of plant infected with control viral particles. In other embodiments, the methods further comprise the steps of The method of Claim 84, further comprising the steps of isolating viral particles from the systemic lesions, the viral particles comprising a genome; and sequencing the genome of the viral particles. In some embodiments, the present invention provides the viral particles produced by the method.

In some embodiments, the present invention provides a vaccine composition comprising a viral particle comprising a capsid having an interior side and an exterior side, the capsid comprising at least one exogenous peptide, wherein the exogenous peptide is on the interior side of the capsid. In further embodiments, the present invention provides methods of inducing a humoral immune response which comprises administering to an animal the vaccine composition.

In still other embodiments, the present invention provides methods of enhancing an immune response to a B cell epitope comprising providing i) a modified viral particle comprising a B cell epitope and an internal CTL epitope in an immunogenic complex; and ii) an animal; and administering the modified viral particle to the animal. The present invention is not limited to and particular CTL epitope. Indeed, a variety of CTL epitopes are contemplated including, but not limited to, a 2F10 peptide mimotope of the class "a" determinant of the hepatitis B virus surface antigen.

The present invention also provides methods of enhancing an immune response to a B cell epitope comprising providing i) a modified viral particle comprising a B cell epitope and an internal CTL epitope in an antigenic complex; and an animal; and b) administering the modified viral particle to the animal. The present invention is not limited to and particular CTL epitope. Indeed, a variety of CTL epitopes are contemplated including, but not limited to, a 2F10 peptide mimotope of the class "a" determinant of the hepatitis B virus surface antigen.

In some embodiments, the present invention provides methods of enhancing an immune response to a B cell epitope comprising providing i) a modified viral particle comprising a B cell epitope and an internal helper T cell epitope in an immunogenic complex; and ii) an animal; and administering the modified viral particle to said animal. The present invention is not limited to any particular T cell epitope. Indeed, a variety of T cell epitopes are contemplated, including, but not limited to the universal T helper epitope of tetanus toxoid.

In further embodiments, the present invention provides methods of enhancing an immune response to a B cell epitope comprising providing i) a modified viral particle comprising a B cell epitope and an internal helper T cell epitope in an antigenic complex; and ii) an animal; and administering the modified viral particle to the animal. The present invention is not limited to any particular T cell epitope. Indeed, a variety of T cell epitopes are contemplated, including, but not limited to the universal T helper epitope of tetanus toxoid.

BRIEF DESCRIPTION OF THE DRAWINGS

FIG. 1 shows the sequence of the N-terminus of the VP-S protein of CPMV and illustrates where foreign peptides can be inserted.

FIG. 2 shows the results of a CTL assay for mice vaccinated with chimeric virus particles according to one embodiment of the invention (see Example 6); the chromium release from target cells charged with the target peptide derived from LCMV or uncharged cells is measured using a BetaMax workstation.

FIG. 3 shows a restriction map of the vector pCP26 used in the majority of genetic constructions disclosed.

DESCRIPTION OF THE INVENTION

The present invention relates to the expression of peptides on viral particles, and more particularly to the expression of peptides on the interior or the viral capsid. The use of chimeric viral particles (CVP's) as vaccines represents an attractive strategy for improving vaccine storage and delivery. The use of CVPs is described in U.S. Pat. Nos. 5,874,087 and 5,958,422 (each of which incorporated herein by reference). These patents describe the development of vectors encoding modified Cowpea Mosaic Virus (CPMV) genomes containing peptide inserts in the coat protein. The vectors are useful for the production of viral particles in which the peptide is presented on the surface of the viral particle.

After the definitions, viral particle expression systems, peptide inserts and sites for insertion, and uses for modified viral particles are described.

Definitions

To facilitate understanding of the invention, a number of terms are defined below.

The term "viral particle" as used herein refers to the fully or partially assembled capsid of a virus. A viral particle may or may not contain nucleic acid.

The term "viral capsid" as used herein refers to the protein coat that surrounds the viral nucleic acid in a wild-type virus. Viral capsids have interior surfaces and exterior surfaces. The interior surface of a viral capsid is the surface that is normally exposed to the viral nucleic acid. The exterior surface of a viral capsid is the surface that is generally exposed to the environment.

The term "viral coat protein" as used herein refers to a protein that interacts with other proteins to assemble and form part of the viral capsid. Examples of viral coat proteins include, but are not limited to, the VP-S and VP-L coat proteins of cowpea mosaic virus. The interior side of a viral coat protein is the portion of the coat protein that is exposed on the interior surface of the viral capsid. The exterior side of a viral coat protein is the portion of the coat protein that exposed on the exterior surface of the viral capsid.

The term "(+) stranded RNA virus" as used herein refers to a virus having an RNA genome, wherein the isolated RNA is directly infectious when introduced to an appropriate host. (+) stranded RNA viruses are known to infect a variety of animal, fungus, and plant hosts. Examples of (+) stranded RNA viruses include, but are not limited to, Picornoviruses (for example, polioviruses), and viruses from the following families: Caulimoviridae, Bromoviridae, Comoviridae, Geminiviridae, Reoviridae, Partitiviridae, Sequiviridae, Tobamoviruses, and Tombusviridae.

The term "symptoms" when used in reference to plant virus infection refers to the appearance of indicators of viral infection in the plant. These indicators are both local lesions and systemic symptoms. Local lesions such as necrotic lesions, chlorotic lesions, and ringspot occur at or near the site of infection. Systemic symptoms appear throughout the plant and include mosaic patterns, mottled patterns, dwarfing, yellowing and necrosis.

The term "systemic infection" as used herein refers to viral infections that spread from the site of initial infection.

In plants, systemic infection occurs when the viruses move from infected cells into the vasculature (for example, phloem) of the plant. In many viruses, this movement is mediated by a movement protein which modifies the plasmadesmata.

The term "icosahedral," when used in reference to viral capsid or viral particle refers to a capsid exhibiting general icosohedral symmetry: 5-fold rotational symmetry through each of 12 apexes, 3-fold rotational symmetry about an axis through the center of each of 20 triangular faces, and 3-fold rotational symmetry about an axis through the center of each of thirty edges. Icosohedrons are comprised of 60 identical building units (which may comprise more than one subunit) or multiples of 60 identical building units. The interunit contacts are not precisely identical throughout the capsid; however, all interunit bonding involves the same general type of contact so that the interunit bonds can be described as quasi-equivalent. It is contemplated that some icosohedral viruses, especially large icosohedral viruses (for example, adenoviruses) may deviate from the structural and geometrical criteria observed by smaller icosohedral viruses. Examples of icosohedral viruses include, but are not limited to, polioviruses, adenoviruses, and viruses from the following families: Caulimoviridae, Bromoviridae, Comoviridae, Geminiviridae, Reoviridae, Partitiviridae, Sequiviridae, and Tombusviridae.

The term "epitope" as used herein refers to an antigenic determinant, which is any region of a macromolecule with the ability or potential of binding to a specific immunoglobulin or T-cell receptor.

The term "hydrophobic," when used in reference to a peptide or epitope, refers to a peptide or epitope having about 20 percent or greater hydrophobic amino acids residues (for example, alanine, valine, leucine, isoleucine, proline, phenylalanine, tryptophan, and methionine).

The term "cytotoxic T-lymphocyte epitope" as used herein refers to an epitope that is capable of recognition by a cytotoxic T-lymphocyte.

The term "helper T-cell epitope" as used herein refers to an epitope that is capable of recognition by a helper T-cell.

The term "B-cell epitope" as used herein refers to an epitope that is capable of recognition by a B-cell.

The term "immune response" as used herein refers to an animal's reaction mediated by the immune system to an antigen or immunogen and may be characterized by the production of antibodies and/or the stimulation of cell-mediated immunity or immune tolerance.

The term "antigenic complex" as used herein refers to complex containing at least one epitope that is capable of combining with an immunoglobulin or cell-surface receptor.

The term "immune complex" as used herein refers to a complex containing at least one epitope that is capable of eliciting a humoral and/or cell-mediated immune response.

The term "mimotope" as used herein refers to a peptide sufficiently structurally similar to an epitope to induce an immune reaction against that epitope even though the two sequences share little or no homology or similarity at the amino acid level (in the case of a peptide mimotope), or, where in the case where the mimotope represents a structural configuration adopted by a non-proteinaceous molecule such as a carbohydrate, the mimotope is capable of reacting with immune molecules directed against that non-proteinaceous epitope.

As used herein, the term "immunoglobulin" refers to the secreted product of plasma cell (for example, activated B-cell) comprising two heavy chain polypeptides complexed with two light chain polypeptides which together make a binding site for proteins or other antigens.

As used herein, the term "MHC Class I-major histocompatibility group I proteins" refers to proteins encoded by the major histocompatibility group genes and which are implicated in the effective presentation of antigens to CD8+ T lymphocytes.

As used herein, the term "MHC Class II— major histocompatibility group II proteins" refers to proteins encoded by the major histocompatibility group genes and which are implicated in the effective presentation of antigens to CD4+ T lymphocytes.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (for example, single cells, protoplasts, embryos, callus, etc.). Plant tissue may be in planta, in organ culture, tissue culture, or cell culture.

The term "protoplast" as used herein refers to isolated plant cells in which the cell walls have been removed. In general, protoplasts are produced in accordance with conventional methods (See, for example, U.S. Pat. Nos. 4,743, 548; 4,677,066, 5,149,645; and 5,508,184; all of which are incorporated herein by reference). Plant tissue may be dispersed in an appropriate medium having an appropriate osmotic potential (for example, 3 to 8 wt. percent of a sugar polyol) and one or more polysaccharide hydrolases (for example, pectinase, cellulase, etc.), and the cell wall degradation allowed to proceed for a sufficient time to provide protoplasts. After filtration the protoplasts may be isolated by centrifugation and may then be resuspended for subsequent treatment or use. Regeneration of protoplasts kept in culture to whole plants is performed by methods known in the art (See, for example, Evans et al., *Handbook of Plant Cell Culture*, 1: 124–176, MacMillan Publishing Co., New York [1983]; Binding, *Plant Protoplasts*, p. 21–37, CRC Press, Boca Raton [1985],) and Potrykus and Shillito, *Methods in Enzymology*, Vol. 118, Plant Molecular Biology, A. and H. Weissbach eds., Academic Press, Orlando [1986]).

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

"Nucleoside", as used herein, refers to a compound consisting of a purine [guanine (G) or adenine (A)] or pyrimidine [thymine (T), uridine (U), or cytidine (C)] base covalently linked to a pentose, whereas "nucleotide" refers to a nucleoside phosphorylated at one of its pentose hydroxyl groups.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; that is, a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a nucleic acid at which a new linkage would be to a 5' carbon is its 5' terminal nucleotide. The end of a nucleic acid at which a new linkage would be to a 3' carbon is its 3' terminal nucleotide. A terminal nucleotide, as used herein, is the nucleotide at the end position of the 3'- or 5'-terminus. DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (that is, altered characteristics) when compared to the wild-type gene or gene product. It is noted that naturally-occurring mutants can be isolated; these are identified by the fact that they have altered characteristics when compared to the wild-type gene or gene product.

As used herein, the term "overexpression" refers to the production of a gene product in transgenic organisms that exceeds levels of production in normal or non-transformed organisms. As used herein, the term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

The term "nucleotide sequence of interest" refers to any nucleotide sequence, the manipulation of which may be deemed desirable for any reason (for example, confer improved qualities), by one of ordinary skill in the art. Such nucleotide sequences include, but are not limited to, coding sequences of structural genes (for example, reporter genes, selection marker genes, oncogenes, drug resistance genes, growth factors, etc.), and non-coding regulatory sequences which do not encode an mRNA or protein product, (for example, promoter sequence, polyadenylation sequence, termination sequence, enhancer sequence, etc.).

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (for example, TAA, TAG, TGA). In some cases the coding region is also known to initiate by a nucleotide triplet "TTG".

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

A "complement" of a nucleic acid sequence as used herein refers to a nucleotide sequence whose nucleic acids show total complementarity to the nucleic acids of the nucleic acid sequence.

The term "homology" when used in relation to nucleic acids refers to a degree of complementarity. There may be partial homology or complete homology (that is, identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.).

A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (that is, the hybridization) of a sequence which is completely homologous to a target under conditions of low stringency.

This is not to say that conditions of low stringency are such that non-specific binding is permitted; low stringency conditions require that the binding of two sequences to one another be a specific (that is, selective) interaction. The absence of non-specific binding may be tested by the use of a second target which lacks even a partial degree of complementarity (for example, less than about 30 percent identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1 percent SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5× SSPE, 0.1 percent SDS at 42° C. when a probe of about 500 nucleotides in length is employed.

High stringency conditions when used in reference to nucleic acid hybridization comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5 percent SDS, 5× Denhardt's reagent and 100 µg/ml denatured salmon sperm DNA followed by washing in a solution comprising 0.1× SSPE, 1.0 percent SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

As used herein, the terms "exogenous peptide" or "foreign peptide" refers to a peptide that is not in its natural environment (that is, has been altered by the hand of man). For example, an exogenous peptide gene includes a peptide that has been inserted into another polypeptide or added or fused to a polypeptide.

As used herein in reference to an amino acid sequence or a protein, the term "portion" (as in "a portion of an amino acid sequence") refers to fragments of that protein. The fragments may range in size from four amino acid residues to the entire amino acid sequence minus one amino acid.

As used herein, the term "fusion protein" refers to a chimeric protein containing the protein of interest (for example, viral coat protein) joined to an exogenous protein fragment (for example, a hydrophobic epitope).

The term "isolated" when used in relation to a nucleic acid, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising SEQ ID NO:X includes, by way of example, such nucleic acid sequences in cells which ordinarily contain SEQ ID NO:X where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (that is, the nucleic acid sequence may be single-stranded). Alternatively, it may contain both the sense and anti-sense strands (that is, the nucleic acid sequence may be double-stranded).

As used herein, the term "purified" refers to molecules or aggregations of molecules (for example, viral particles), either nucleic or amino acid sequences, that are removed from their natural environment, isolated or separated. An "isolated nucleic acid sequence" is therefore a purified nucleic acid sequence. "Substantially purified" molecules are at least 60 percent free, preferably at least 75 free, and more preferably at least 90 percent free from other components with which they are naturally associated.

As used herein, the terms "vector" and "vehicle" are used interchangeably in reference to nucleic acid molecules that transfer DNA segment(s) from one cell to another. Vectors may include plasmids, bacteriophages, viruses, cosmids, and the like.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences.

Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (that is precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap, Plant Mol. Biol. 24:119–127 [1994]) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (for example, heat shock, chemicals, light, etc.) which is different from the level of transcription of the operably linked nucleic acid sequence in the absence of the stimulus.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (that is, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory*

*Manual,* 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6–16.7).

The terms "infecting" and "infection" with a bacterium refer to co-incubation of a target biological sample, (for example, cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, Bio-Rad).

The term "microwounding" when made in reference to plant tissue refers to the introduction of microscopic wounds in that tissue. Microwounding may be achieved by, for example, particle bombardment as described herein or by abrading the tissue. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "foreign gene" refers to any nucleic acid (for example, gene sequence) which is introduced into the genome of a cell by experimental manipulations and may include gene sequences found in that cell so long as the introduced gene contains some modification (for example, a point mutation, the presence of a selectable marker gene, etc.) relative to the naturally-occurring gene.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (for example, β-glucuronidase) encoded by the transgene. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

A. Viral Particle Expression Systems

To produce modified virus particles in accordance with this invention the viral nucleic acid is modified by introducing a nucleotide sequence coding for the foreign peptide (for example, an animal virus antigen) at that part of the viral genome which codes for a portion of the coat protein exposed to the interior of the viral capsid, infecting host cells or organisms with the modified viral nucleic acid, and harvesting assembled particles of the modified virus. This procedure is best carried out by direct manipulation of the DNA of the virus in the case of DNA viruses or by manipulation of a cDNA corresponding to the RNA of an RNA virus. Accordingly, in some embodiments, the present invention provides vectors encoding a viral particle that has been modified so as to express an exogenous or foreign peptide on the interior surface of the viral capsid. In particularly preferred embodiments, the nucleic acid sequence encoding a viral coat protein is modified by inserting a sequence encoding an exogenous peptide, so that when the viral coat protein is assembled into a capsid, the exogenous peptide is presented on the interior surface of the capsid. In further embodiments, the sequence encoding the exogenous peptide is inserted in a portion of the viral coat protein so that assembly of the viral coat protein into a capsid is not substantially interfered with or disrupted.

A wide variety of viral particles find use in the present invention. It is contemplated that both DNA and RNA viruses are suitable for modification be the methods described herein. In particularly preferred embodiments, the modified viral particle is a plant virus. In further preferred embodiments, the plant viruses are preferably icosahedral viruses. To date, all plant viruses with icosahedral symmetry for which crystal structures have been elucidated are characterized by the presence of a canonical eight stranded β-barrel conformation. It is therefore likely that this is a configuration common to all plant icosahedral viruses. Thus, a preferred icosahedral plant virus may be selected from the following virus families: Caulimoviridae, Bromoviridae, Comoviridae, Geminiviridae, Reoviridae, Partitiviridae, Sequiviridae, and Tombusviridae; and the following virus genera: Luteovirus, Marafiviris, Sobemovirus, Tymovirus, Enamovirus, and ideavirus.

In particularly preferred embodiments, the modified viral particle is from the family Comoviridae. Comoviruses are a group of at least fourteen plant viruses which predominantly infect legumes. Their genomes consist of two molecules of single-stranded, positive-sense RNA of different sizes which are separately encapsidated in isometric particles of approximately 28 nm diameter. The two types of nucleoprotein particles are termed middle (M) and bottom (B) component as a consequence of their behavior in caesium chloride density gradients, the RNAs within the particles being known as M and B RNA, respectively. Both types of particle have an identical protein composition, consisting of 60 copies each of a large (VP37; VP-L) and a small (VP23; VP-S) coat protein. In addition to the nucleoprotein particles, comovirus preparations contain a variable amount of empty (protein-only) capsids which are known as top (T) component.

In the case of the type member of the comovirus group, cowpea mosaic virus (CPMV), it is known that both M and B RNA are polyadenylated and have a small protein (VPg) covalently linked to their 5' terminus. More limited studies on other comoviruses suggest that these features are shared by the RNAs of all members of the group. Both RNAs from CPMV have been sequenced and shown to consist of 3481 (M) and 5889 (B) nucleotides, excluding the poly (A) tails (van Wezenbeek et al., EMBO J. 2:941–46 [1983]; Lomonossoff and Shanks, EMBO J. 2:2253–2258 [1983]). Both RNAs contain a single, long open reading frame, expression of the viral gene products occurring through the synthesis and subsequent cleavage of large precursor polypeptides. Though both RNAs are required for infection of whole plants, the larger B RNA is capable of independent replication in protoplasts, though no virus particles are produced in this case (Goldbach et al., Nature 286:297–300 [1980]). This observation, coupled with earlier genetic studies, established that the coat proteins are encoded by M RNA.

A 3.5 angstrom electron density map of CPMV shows that there is a clear relationship between CPMV and the T=3 plant viruses such as the tombusviruses, in particular tomato bushy stunt (TBSV) and the sobemoviruses, in particular southern bean mosaic (SBMV). The capsids of these latter viruses are composed of 180 identical coat protein subunits, each consisting of a single β-barrel domain. These can occupy three different positions, A, B and C, within the virions. The two coat proteins of CPMV were shown to consist of three distinct β-barrel domains, two being derived from VP37 and one from VP23. Thus, in common with the T=3 viruses, each CPMV particle is made up of 180 β-barrel structures. The single domain from VP23 occupies a position analogous to that of the A-type subunits of TBSV and SBMV, whereas, the N- and C-terminal domains of VP37 occupy the positions of the C and B type subunits respectively.

X-ray diffraction analysis of crystals of CPMV and another member of the group, bean pod mottle virus (BPMV) shows that the 3-D structures of BPMV and CPMV are very similar and are typical of the comovirus group in general. In the structures of CPMV and BPMV, each β-barrel consists principally of 8 strands of antiparallel β-sheet connected by loops of varying length. The flat β-sheets are named the B, C, D, E, F, G, H and I sheets, and the connecting loops are referred to as the βB-βC, βD-βE, βF-βG and βH-βI loops.

The comoviruses are also structurally related to the animal picornaviruses. The capsids of picornaviruses consist of 60 copies of each of three different coat proteins VP1, VP2 and VP3 each one consisting of a single β-barrel domain. As in the case of comoviruses, these coat proteins are released by cleavage of a precursor polyprotein and are synthesised in the order VP2-VP3-VP1. Comparison of the 3-dimensional structure of CPMV with that of picornaviruses has shown that the N- and C-terminal domains of VP37 are equivalent to VP2 and VP3 respectively and that VP23 are equivalent to VP1. The equivalence between structural position and gene order suggests that VP37 corresponds to an uncleaved form of the two picornavirus capsid proteins, VP2 and VP3.

One of the principal differences between the comoviruses and picornaviruses is that the protein subunits of comoviruses lack the large insertions between the strands of the β-barrels found in picornaviruses though the fundamental architecture of the particles is very similar. The four loops (βB-βC, βD-βE, βF-βG and βH-βI) between the β-sheets are not critical for maintaining the structural integrity of the virions but, in accordance with this invention, are used as sites of expression of foreign peptide sequences, such as antigenic sites from animal viruses.

An advantage of Comoviridae is that the capsid contains 60 copies of each of two constituent coat proteins, thereby permitting 60–180 copies of a peptide to be presented per virion wherein the individual coat protein domains have been manipulated such they express inserted peptides. Within the family Comoviridae, cowpea mosaic virus and bean pod mottle virus are preferred; of these cowpea mosaic virus is the most preferred.

CPMV is a bipartite RNA virus and in order to manipulate the genome of any RNA virus to express foreign peptides it is desirable to use cDNA clones of the RNA. Accordingly, in some embodiments, the present invention provides cDNA vectors that encode a viral particle modified to express an exogenous peptide on the interior of the viral capsid. Full length cDNA clones of both CPMV RNA molecules are available which can be manipulated to insert oligonucleotide sequences encoding an exogenous peptide. In some particularly preferred embodiments, the vector is pCP26. In other embodiments, the vector contains B RNA or M RNA or a variant or homolog of B RNA or M RNA. In some embodiments, the variant or homolog is capble of hybridizing to a plus or minus strand of B RNA or M RNA under conditions of high to low stringency. In particulat preferred embodiments, the variant or homolog contains a sequence encoding an exogenous peptide.

In some embodiments, the cDNA is used to generate in vitro transcripts that are infectious when inoculated onto plants. Accordingly, in some embodiments, the present invention provides RNA vectors that encode a viral particle modified to express an exogenous peptide on the interior of the viral capsid. However, the infectivity of the transcripts is significantly lower than that of natural virion RNAs, probably as a result of the presence of non-viral residues at the termini of the transcripts. Difficulties may also be caused by exposure of the transcripts to degradative agents during inoculation. For this reason the transcripts are usually stabilized by capping their 5' ends. In still further preferred embodiments, the modified viral particles also include an exogenous peptide that is presented on the exterior surface the viral capsid. Methods for presenting exogenous peptides on the exterior of the viral capsid are provided in U.S. Pat. Nos. 5,874,087 and 5,958,422, each of which incorporated herein by reference.

In further embodiments, the cDNA is used to directly inoculate plants. In these embodiments, the sequences encoding the modified viral particle are operably linked to a promoter that is expressed in plant tissue. Promoters that find use in the present invention include, but are not limited to, the Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap, Plant Mol. Biol. 24:119–127 [1994]) promoters. This technique overcomes some of the problems encountered with the use of transcripts generated in vitro and is applicable to all plant RNA viruses.

In the case of a DNA virus, the DNA itself is introduced into the plant. In this way, the foreign peptide is initially expressed as part of the capsid protein and is thereby produced as part of the whole virus particle. The peptide may thus be produced as a conjugate molecule intended for use as such. Alternatively, the genetic modification of the virus may be designed in order to permit release of the desired peptide by the application of appropriate agents which will effect cleavage from the virus particle.

In order to produce modified virus on a commercial scale, it is not necessary to prepare infective inoculant (DNA or RNA transcript) for each batch of virus production. In some embodiments, an initial inoculant may be used to infect plants and the resulting modified virus may be passaged in the plants to produce whole virus or viral RNA as inoculant for subsequent batches.

In some embodiments, the viral capsid does not contain nucleic acid. Methods are known in the art for the selective enrichment and purification of "empty" virions (See for example, van Kammen and de Jaeger, Cowpea Mosaic Virus, In: CMI/AAB Description of Plant Viruses 197, Commonwealth Agricultural Bureax [1978]; and WO 98/56933, the disclosure of which is incorporated herein by reference).

B. Expression of Exogenous Peptides on the Interior of Viral Capsid

One of the limitations of previously described viral expression technologies is the fact that positively charged peptides or hydrophobic peptides inserted in one of the surface loops of the coat proteins eliminate viral infectivity, due to a disturbed protein folding, particle aggregation, or a disturbed viral transport. The non-viability of these particles is a great hindrance for the expression of some epitopes. Positively charged epitopes can be compensated for by the expression of some additional acidic amino acids (for example, pIMM8, pIMM9; Bendalm-nane et al., J. Mol. Biol. 290(1):9–20 [1999]). The expression of hydrophobic residues on the surface, however, has so far been very difficult. The use of alternative insertion sites on the virus surface does not solve the problem. The insertion of epitopes in the C-terminus of VP-S, which is on the surface as well, in general gives similar characteristics. This limitation of the technology makes it difficult to express most T-cell epitopes. The discovery of new insertion sites is described below.

1. Insertion Sites

In general, the exogenous RNA or DNA may be inserted into the plant virus genome in a variety of configurations. For example, it may be inserted as an addition to the existing nucleic acid or as a substitution for part of the existing sequence, the choice being determined largely by the structure of the capsid protein and the ease with which additions or replacements can be made without interference with the capacity of the genetically-modified virus to assemble in plants. Determination of the permissible and most appropriate size of addition or deletion for the purposes of this invention may be achieved in each particular case by experiment in the light of the present disclosure. The use of addition inserts appears to offer more flexibility than replacement inserts in some instances.

The present invention demonstrates the insertion of epitopes in viral coat proteins so that they are expressed on the interior surface or side of a viral capsid. In general, any portion of a viral coat protein that is exposed on the interior surface of an assembled viral capsid is a candidate site for epitope insertion. In some embodiments of the present invention, such sites are selected by analysis of high resolution structures (for example, crystal structure analysis) of viral capsids. In further embodiments of the present invention, the viral coat protein is modified at the identified site by inserting an epitope. Vectors (for example, cDNA or RNA vectors) encoding the modified virus are then used to infect an appropriate host (for example, protoplasts, plant tissue, or whole plants). If infection occurs (for example, as assayed by the appearance of local lesions in a plant), then the site is useful for the expression of an epitope. In some instances, serial selection of the infectious virus identifies mutations leading to greater infectivity, including viral particles capable of systemic infection (discussed in more detail below).

The present invention is exemplified by the insertion of a foreign peptide into VP-S of CMPV. In some embodiments, the site of insertion is the N-terminus of VP-S. In further embodiments, the foreign peptide is inserted at a point between 5 and 20 amino acids from the N-terminus, preferably between 7 and 15 amino acids from the N-terminus, and more preferably between 9 and 12 amino acids from the N-terminus. In preferred embodiments, insertion of the foreign peptide does not perturb the function (for example, assembly) of the virus in vivo.

The N-terminus is, according to the high resolution structure, on the inside of the virion, rather then on the outer surface. The present invention is not limited to a particular mechanism of action. Indeed, an understanding of the mechanism of action is not necessary to practice the invention. Nevertheless, as a strategy for the expression of epitopes in the N-terminus of VP-S of CPMV, it appears to be desirable to insert the epitope between a duplication of Y11 or V10Y11. The N-terminus plays a role in the viral life cycle, since it is recognized by the viral protease during polyprotein processing. The exact size of the recognition site is not known, but in analogy to the recognition site in between the VP37 and the MP (movement protein) it is probably 10–11 amino acids (Verver et al., Virology 242: 22–27 [1998]). The first 10 amino acids of VP-S project from the β-barrel of VP-S, and do not interact with any other residues. Y11 marks the boundary between the N-terminus of VP-S and the rest of the small coat protein and is in a hydrophobic pocket formed by Q73, R165 and H71. Insertion at Y11 apparently does not disrupt polyprotein processing.

Other factors also make this a desirable site. The RNA-distribution inside CPMV is unknown. However, in the middle component of bean pod mottle comovirus, some RNA is observed in the crystal structure. The main RNA-protein interactions take place at the N-terminus of the VP37. This may as well be the case for CPMV. Cryo E.M. pictures of CPMV show that there probably is a small empty space at the five fold symmetry axes, just beneath the protein shell. Furthermore, the N-terminus of VP-S contains two negatively charged residues, which makes an interaction with the sugar-phosphate backbone of the RNA very unlikely as well. Therefore, insertion in the N-terminus of VP-S is unlikely to interfere with RNA interactions and a space exists to accomodate the foreign peptide. Additionally, the N-terminus of VP-S is probably well structured, and the five termini of symmetry related VP23 molecules in the virion form an annulus (Lin et al., Journal of Virology 74(1): 493–504 [1999]). The B factors indicate that amino acids 1–9 are flexible. Insertions in this region will most likely disturb the annulus, but will probably not affect the folding of the βbarrel. It may be relevant that pepscan experiments indicate that the N-terminus of VP-S in CMPV and in a number of other icosahedral plant viruses represents one of the strongest B-cell epitopes. This is consistent with the notion that this domain (normally buried within the capsid) is temporally exposed through the dynamic behavior (that is, "breathing") of the assembled virion.

Accordingly, in some embodiments, the present invention provides a modified CPMV having a foreign peptide inserted at Y11. In still further embodiments, the foreign peptide is inserted between a duplication of Y11 of VP-S. In other embodiments, the present invention provides a modified CPMV having a foreign peptide inserted between a duplication of V10Y11 of VP-S. The present invention is not limited to any particular mechanism of action. Indeed, an understanding of the mechanism of action is not necessary to practice the invention. However, it is contemplated that flanking a foreign peptide with a duplication of Y11 or V10Y11 preserves the hydrophobic context of Y11.

The duplication of Y 11 represents an engineered modification of the viral vector which has been made to facilitate the accommodation of foreign peptides within the capsid of CPMV. In general, other changes to the amino acid sequence of CPMV have proved difficult to design since many observed de novo mutations that occur on particles displaying peptides on the outer aspect of the particle have been limited to changes within the foreign peptide itself.

Several epitopes were successfully inserted at the Y11 position, giving reasonable to very good infection on cowpea plants. Several constructs had a duplication of V10Y11, which in two cases (pNLAL7/pMAL8 and pMV14/pMV15) turned out to be useful to avoid mutations in the epitope or to make the construct infectious. In one construct (pTr4), only V10 was duplicated (because the epitope begins and ends with Val) and also in this case the construct was infectious. These results make it advisable to duplicate at least V10 and if possible V10Y11 in new constructs.

2. Peptides

The foreign peptides which may be incorporated into plant viruses according to this invention may be of highly diverse types and are subject only to the limitation that the nature and size of the foreign peptide and the site at which it is placed in or on the virus particle do not interfere with the capacity of the modified virus to assemble when cultured in vitro or in vivo. In broad concept, modified viruses may be formed from any biologically useful peptides (usually polypeptides) the function of which requires a particular conformation for its activity. This may be achieved by association of the peptide with a larger molecule (for example, to improve its stability) or mode of presentation in a particular biological system. Examples of such peptides are peptide hormones; enzymes; growth factors; antigens of protozoal, viral, bacterial, or fungal origin; antibodies including anti-idiotypic antibodies; immunoregulators and cytokines (for example, interferons and interleukins); receptors; adhesins; and parts or precursors of any of the foregoing types of peptide. The peptide preferably contains more than 5 amino acids.

The present invention allows for the expression of wide variety of foreign peptides on the interior surface of viral capsids. In some embodiments, the peptide is from 5–20 amino acids, preferably from 7–15 amino acids, and most preferably from 8–12 amino acids. However, it is contemplated that the limit on foreign size be limited only by the chimeric virus's capacity to accomodate a foreign peptide and still be capable of assembly into an infectious virus in planta. In preferred embodiments, the foreign peptide has immunological properties. Accordingly, in some embodiments, the foreign peptide is an antigen or immunogen. Examples of the epitopes that have been successfully inserted are provided in Table 1 below. In some embodiments, the epitope is a B-cell epitope. In other embodiments, the epitope is a T-cell epitope. In some preferred embodiments, the foreign peptide is a cytotoxic T lymphocyte epitope which is reactive towards cytotoxic T lymphocytes. In general, T-cell epitopes are hydrophobic. In some embodiments, the epitopes have a pI of greater than 7.0 (for example, pHBV16, pLCMV2, PVSVI) and are hydrophobic or contain long hydrophobic stretches (for example, pLCMV2 and pHBV16). Some of these epitopes had previously been inserted in the βBβC-loop of VP-S, giving good (short HBV epitope), moderate (LCMV epitope), or no (2F10 peptide) symptoms. In some preferred embodiments, the peptide corresponds to SEQ ID NOs: 4–17. In other embodiments, the peptide is encoded by a nucleic acid sequence corresponding to SEQ ID NOs: 18–31.

TABLE 1

Summary of N-terminal Inserts

| Construct | N-terminus of VP-S | Insert Amino Acid Sequence | Insert Nucleic Acid Sequence | βA |
|---|---|---|---|---|
| CPMV | SEQ ID NO: 1<br>GPVCAEASDV | | | SEQ ID NO: 31<br>YSPCMIAST |
| PHBV 15 | SEQ ID NO: 2<br>GPVCAEASDVY | SEQ ID NO: 4<br>GYHGSSL | SEQ ID NO: 18<br>ggttatcatggttctagtttg | SEQ ID NO: 31<br>YSPCMIAST |

TABLE 1-continued

Summary of N-terminal Inserts

| Construct | N-terminus of VP-S | Insert Amino Acid Sequence | Insert Nucleic Acid Sequence | βA |
|---|---|---|---|---|
| PHBV 16 | SEQ ID NO: 2 GPVCAEASDVY | SEQ ID NO: 5 AVYYCTRGYHG SSL | SEQ ID NO: 19 gctgtttattattgtactaga ggttatcatggttctagtttg | SEQ ID NO: 31 YSPCMIAST |
| PLCMV 2 | SEQ ID NO: 2 GPVCAEASDVY | SEQ ID NO: 6 RPQASGVYMGN LTAQ | SEQ ID NO: 20 agacctcaagcttctggtgt ttatatgggtaatttgactgc tcaa | SEQ ID NO: 31 YSPCMIAST |
| PMAL 7 | SEQ ID NO: 2 GPVCAEASDVY | SEQ ID NO: 7 SYIPSAEKI SEQ ID NO: 8 SYIPSAGKI* | SEQ ID NO: 21 tcttatattccttctgctgaaa agatt | SEQ ID NO: 31 YSPCMIAST |
| PMAL 8 | SEQ ID NO: 2 GPVCAEASDVY | SEQ ID NO: 7 SYIPSAEKI | SEQ ID NO: 21 tcttatattccttctgctgaaa agatt | SEQ ID NO: 32 VYSPCMIAST |
| PMAL 10 | SEQ ID NO: 2 GPVCAEASDVY | SEQ ID NO: 7 SYIPSAEKI | SEQ ID NO: 21 tcttatattccttctgctgaaa agatt | SEQ ID NO: 32 VYSPCMIAST |
| PMAL 11 | SEQ ID NO: 2 GPVCAEASDVY | SEQ ID NO: 9 AAASYIPSAEKIA AAA | SEQ ID NO: 22 gcagcggcctcttatattcc ttctgctgaaaagattgcgg ccgctgct | SEQ ID NO: 32 VYSPCMIAST |
| pSEN 1 | SEQ ID NO: 2 GPVCAEASDVY | SEQ ID NO: 10 APGNYPAL | SEQ ID NO: 23 gctcctggtaattatcctgct ttg | SEQ ID NO: 31 YSPCMIAST |
| pSEN 2 | SEQ ID NO: 2 GPVCAEASDVY | SEQ ID NO: 11 HGEFAPGNYPAL WSYA | SEQ ID NO: 24 catggtgaatttgctcctggt aattatcctgctttgtggtctt atgct | SEQ ID NO: 31 YSPCMIAST |
| pSEN 3 | SEQ ID NO: 2 GPVCAEASDVY | SEQ ID NO: 11 HGEFAPGNYPAL WSYA | SEQ ID NO: 24 catggtgaatttgctcctggt aattatcctgctttgtggtctt atgct | SEQ ID NO: 31 YSPCMIAST |
| pVSV1 | SEQ ID NO: 2 GPVCAEASDVY | SEQ ID NO: 12 RGYVYQGL | SEQ ID NO: 25 agaggttatgtttatcaagg ttg | SEQ ID NO: 31 YSPCMIAST |
| pMV 14 | SEQ ID NO: 2 GPVCAEASDVY | SEQ ID NO: 13 LDRLVRLIG | SEQ ID NO: 26 ttggatagattggttagattg attggt | SEQ ID NO: 31 YSPCMIAST |
| pMV 15 | SEQ ID NO: 2 GPVCAEASDVY | SEQ ID NO: 13 LDRLVRLIG | SEQ ID NO: 26 ttggatagattggttagattg attggt | SEQ ID NO: 32 VYSPCMIAST |
| pMV 16 | SEQ ID NO: 2 GPVCAEASDVY | SEQ ID NO: 14 AAALDRLVRLIG AAA | SEQ ID NO: 27 gcagcggccttggatagat tggttagattgattggggcc gctgct | SEQ ID NO: 32 VYSPCMIAST |
| HBV 18 | SEQ ID NO: 2 GPVCAEASDVY | SEQ ID NO: 16 MQWNSTTFHQT LQ | SEQ ID NO: 29 atgcaatggaactctactac ttttcatcaaactttgcaa | SEQ ID NO: 32 VYSPCMIAST |
| pCP 35 | SEQ ID NO: 2 GPVCAEASDVY | SEQ ID NO: 17 AAAAA | SEQ ID NO: 30 gcagcggccgctgct | SEQ ID NO: 32 VYSPCMIAST |

*A mutation was observed in the epitope of pMAL 7.

The use of the insertion site in the N-terminus of VP-S has clear advantages over insertion sites used before, in that it is now possible to express hydrophobic or basic epitopes. This opens a whole new range of possibilities for the expression of foreign epitopes on CPMV. Since the new insertion site is on the inside of the virus particle, a strong antibody response to the inserted epitope is not likely. However, buried N-termini of many plant viruses turn out to be among the most immunogenic parts of the virus. The most likely explanation for this phenomenon is the dynamic behavior (breathing) of the particles. For this reason, the B-cell response to the 2F10 peptide in HBV16 was tested. The absence of any α-2F10 antibodies clearly indicates that the epitope in this construct is buried.

3. Second Site Mutations

Surprisingly, it has been found that chimeric virus particles containing a foreign peptide in the N-terminus of VP-S (that is, an internal display particle) are particularly prone to selection for mutations affecting the sequence of the coat proteins in planta at sites other than in the insertion itself. These de novo mutations are characterized by the following features: the new mutations occur spontaneously and are selected in the host plant; and a very large proportion of the mutations occur at positions distal and proximal to the insertion site of the foreign peptide. Interestingly, many of the mutations effect changes in the amino acid sequences in the coat proteins located in domains which are thought to be involved in protein—protein interaction between capsid subunits.

By infecting a host plant with a novel chimeric virus particle construct containing an internalized epitope, it is possible to select and isolate novel virus particles in which amino acids other than those present in the insert are altered. Moreover, it is clear that the de novo mutations at a given position in a given coat protein may arise independently time and again leading to separately induced and selected mutations at precisely the same-position in proteins comprising the capsid. In addition, the fact that a given amino acid residue may be altered to different amino acids (that is, non-conservative changes) suggests that it is more important to remove from the structure the constraint exercised by the original amino acid than it is to establish a particular amino acid substitution. Moreover, amino acid substitutions are naturally limited to those resulting from (single) point mutations at non-wobble positions in codons. Hence, a method for identifying positions in the CPMV capsid, permissive for the selection of compensatory mutations ("hotspots") is provided. The method is independent of the internalized peptide expressed and its precise insertion point within such a capsid.

More remarkably still, second site, third site and further mutations can be selected in coat proteins of CPMV by infecting a host plant with a chimaera expressing internally a foreign peptide. Where such third site and further mutations occur, the infectivity and productivity of the novel chimeric virus particle is enhanced over that of its counterpart with only one de novo (second site only) mutation. Moreover, if the genome of the altered virus is used to present a different peptide, both the infectivity and productivity of that virus particle are greater than that seen with the wild type virus vector expressing the same peptide. Thus the invention provides a means of generating improved viral vectors capable of higher productivity in planta than the cognate wild type CPMV vectors.

Accordingly, in some embodiments, the present invention also provides vectors containing second and third site mutations that enhance infectivity of viral particles containing epitope insertions, and methods for selecting such mutations. In some embodiments, the mutations are in VP-S, while in other embodiments, the mutations are in the VP-L. Seven second site mutations and two third site mutations are described in Table 2 below. Accordingly, the present invention also provides a vector bank containing a variety of mutated viral vectors that can be selected for epitope expression. A detailed protocol for the selection and identification of these mutations is provided in Example 12.

TABLE 2

Summary of Mutations

| Mutation in CMPV RNA2 | Mutation in Coat Protein | Construct Mutation Identified In | Constructs Mutations Applied To |
|---|---|---|---|
| T2931C | F91S in VP-S | pMAL8 | pMAL8(=pMAL10) |
| T3199G | F180L in VP-S | pSEN1 | pSEN2(=pSEN3) |
| A3188G | M177V in VP-S | pTT4 | pTT4(=pTT7) |
| A3029G | I124V in VP-S | pTT4, pPAE14 | pTT4(=pTT6) |
| G2388A | R2102K in VP-L | pTT4 | pTT4(=pTT5) |
| A2245G | I2045M in VP-L | pTT4 | — |
| T3189C | M177T in VP-S | pPAE14 | — |
| G2357A | A2092T in VP-L | pMUC53 | — |
| G2898A | G80D in VP-S | pMUC53 | — |

The present invention is not limited to a particular mechanism of action. Indeed, an understanding of the mechanism of action is not necessary to utilize the present invention. Nevertheless, most of the mutated amino acids are probably involved in intermolecular protein—protein interactions. Phe91 is on the interface of two neighboring VP23 molecules. The F91S mutation will definitely weaken this interaction. Phe180 is on the interface of a VP23 and VP37 molecule, and interacts with Phe2045 and Ala2047. The F180L mutation inhibits these interactions. Met177 has a hydrophobic interaction with the side chain of Arg97 of the C-domain of VP37. Both the M177V and the M177T mutation make this interaction impossible. Arg2102 is probably close in space to the N-terminus of a neighboring VP37. There is an intramolecular interaction with E2121, which is impossible when the R2102K mutation takes place. Some of the mutated residues, however, are buried in one of the coat proteins, and the structural consequences are less likely to predict. A possible explanation for at least some of the mutations is that there is a need for a reduced particle stability, to ensure efficient virus decapsidation. Since the N-termini of VP-S form an annulus, the inserted epitopes may interact with one another and stabilize the virion particle. It seems that some epitopes have a much stronger tendency to do this than others. Thus, there is a clear application for the second site mutations. In some embodiments of the present invention, the mutations can be utilized in constructs that by themselves are not infectious (for example, pSEN2, see Table 2 above). It is contemplated that this increases the range of possibilities for the use of the new insertion site. Accordingly, a useful approach is the production of a bank of vectors with all the second and third site mutations that have been observed, in which new epitopes can be cloned. In some embodiments, selection for the most viable vector can then take place in the plant.

4. Expression in Combination with External Epitopes

The present invention also encompasses viral particles and vectors encoding viral particles that express epitopes on the both the interior and exterior of the viral capsid. These particles are called amphidisplay chimeric virus particles (ADCVPs). The present invention is not limited to any particular mechanism of action. Indeed, an understanding of the mechanism is not necessary to practice the invention. Nevertheless, it is contemplated that co-expression of T-cell and B-cell epitopes on the viral particle may lead to an enhanced immune response to the B-cell epitope. Accordingly, in some embodiments, the present invention comprises a viral particle (or vector encoding a viral particle) that expresses a B-cell epitope on the exterior of the viral capsid and a T-cell epitope on the interior of the viral capsid. In some preferred embodiments, the viral particle is CMPV and T-cell epitope is inserted in the N-terminus of VP-S. In still further embodiments, the T-cell epitope is inserted in between a duplication of Y11 or V10Y11, and the B-cell epitope is inserted either in the βBβC loop, the βC'βC" loop, or the carboxyl terminus of VP-S or the βEαB loop of VP-L. Examples of ADVCPs are provided in Example 7.

C. Uses of Modified Viral Particles

The vectors and viral particles of the present invention have many uses. In some embodiments, the viral particles are used to induce either an immunogenic or antigenic response in an animal. Therefore, the viral particles are useful in the protection of animals, including humans, against diseases caused by pathogens. In other embodiments, the particles find use as cancer vaccines. In further embodiments, the viral particles are utilized to make a vaccine composition. In preferred embodiments, the vaccine composition comprise a modified viral particle and an adjuvant (for example, QS-21). The vaccine is then administered to the animal as is known in the art.

EXAMPLES

The following examples serve to illustrate certain preferred embodiments and aspects of the present invention and are not to be construed as limiting the scope thereof. In the disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade); cDNA (copy or complimentary DNA); DNA (deoxyribonucleic acid); ssDNA (single stranded DNA); dsDNA (double stranded DNA); dNTP (deoxyribonucleotide triphosphate); CPMV (Cowpea Mosaic Virus); ADVCP (Amphidisplay chimeric virus particle); CTL (cytoxic T-lymphocyte); CVP (Chimeric Virus particle); ELISA (enzyme-linked immunosorbent assay); MP (Movement Protein); VLP (Virus-Like Particle); VP-L (virus protein-large [37 kDa coat protein]); VP-S (virus protein-small [23 kDa coat protein]).

The vector used in all the experiments described below is pCP26. This is derived from pCP7 described in (Dalsgaard et al., Nat. Biotech. 15, 248–252 [1997]) and consists of: the commercially available vector Bluescript p BS 11 BS SK+ (Stratagene, CA) having cloned into it a cassette comprising the constitutive plant promoter from cauliflower mosaic virus (CAMV 35S) ligated to a cDNA molecule corresponding to RNA2 of infectious cowpea mosaic virus in which the nucleotides encoding the N-terminal 24 amino acids have been deleted and a mutation of nt3295 (T→A), introducing a PstI restriction endonuclease site, has been engineered. In the vector backbone sequence the following point mutations have been engineered to create new restriction endonuclease sites: Eco47III (T→C at nt960) and SalI, (T→C at nt1005). The polylinker sequence has been deleted between SalI and KpnI. Since the majority of the polylinker has been removed in this construct, there is a unique EcoO 1091 restriction site close to the Nhe1 site that is normally used for insertions in the βBβC-loop of the VP-S. This is shown in FIG. 1, which indicates the cloning strategy for the insertion of epitopes in between a duplication of Tyr11 of the VP-S of CPMV. The two restriction sites are used to insert oligonucleotides encoding various epitopes.

Unless otherwise stated, inoculation of host plants with cDNA encoding chimeric virus particles described in the following examples was carried out essentially as outlined in Daisgaard et al., supra, and Dessens & Lomonossoff, J. Gen. Virol. 74, 889–892 [1993]). To achieve the simultaneous expression of combinations of N-terminal plus surface epitopes on VP-S of CPMV, two plasmids each encoding an epitope in a different insertion site are digested with NheI and BamHI, resulting in fragments of 1.3 kb and 5 kb. The smaller fragment contains the sequence encoding the N-terminus of the VP-S, and the larger fragment contains sequences encoding the βBβC-loop, the βB'βC"-loop and the C-terminus of the VP-S. Constructs containing multiple epitopes are made by purifying the fragments containing the inserted epitopes and ligating them together using standard molecular biology techniques (Sambrook, J., Fritsch, E. F. & Maniatis, T. Molecular Cloning—A laboratory manual. 2nd Edition. Cold Spring Harbor Laboratory Press [1989]).

Example 1

This example demonstrates the expression of a peptide on the interior of a viral capsid. In particular, peptides derived from a mimotope of the class "a" determinant of hepatitis B surface antigen are inserted into the VP-S of CPMV. A sequence derived from the anti-idiotypic monoclonal antibody against hepatitis B virus surface antigen (HBsAg), AVYYCTRGYHGSSLY (SEQ ID NO: 33), and a highly hydrophobic octomer derived from this same sequence (GYHGSSLY; SEQ ID NO: 34) are reported to be effective in mounting an immune response cognate with that generated by the "a" determinant of the HBV surface antigen itself (See, for example, U.S. Pat. Nos. 5,531,990; 5,668,253; 5,744,135; and 5,856,087, each of which is incorporated herein by reference). The same peptide generates an HBV-specific T helper response. Thus, the peptide, designated 2FI0, and its derivatives are mimotopes of the "a" determinant. The quindecamer and the octamer derived from 2F10 can be expressed on the external surface of CPMV particles. The octomer is expressed in the βBβC-loop of the VP-S and in the βEαB loop of VP-L (Brennan et al., Microbiology 145: 211–220 [1991]) generating chimeric particles designated respectively, HBV7 and HBV14. Both CVPs are capable of mounting an infection in cowpea plants upon inoculation. The quindecamer can be expressed variously in the βBβC-loop of VP-S to generate a construct known as HBV2; in the C-terminus of VP-S to produce HBV8; and in the βEαB loop of VP-L (HBV3). For these three constructs the symptoms are restricted to the inoculated leaves, even after passage of purified virus to other plants. In other words, there is no selection in planta for chimeric viruses within the population capable of mounting a viable infection cycle.

To overcome this technical limitation both peptides are expressed as distinct insertions in the N-terminus of the VP-S. The octamer (HBV 15) and the quindecamer (HBV 16) are inserted in between Tyr11 and Ser12. This position is chosen because the N-terminus is implicated in the binding of a viral polyprotein protease thought to require at least the ten N-terminal amino acids. Therefore, a desired outcome of inserting a foreign peptide into the N-terminus of VP-S is to avoid ablation of the binding of the protease in order to execute its function. Given that the native N-terminal domain includes a tyrosine residue at position 11, it seems important to maintain the presence of this residue in a contiguous amino acid motif. Since the peptides themselves each terminate with a tyrosine residue, a duplication of Tyr11 is not necessary in order to express them internally in this instance (see also Example 2 below). In all the plants inoculated with cDNA, HBV 15 produces symptoms on the host plant indistinguishable from those produced in a wild type CPMV infection. Particles purified from 62 grams of leaves following a standard procedure for the purification of CPMV Daisgaard et al., supra, yield 64.5 mg. HBV 16 produces symptoms on 3 out of 5 plants inoculated with cDNA. However, in plants that are subsequently inoculated with virus purified from the initial infection cycle, symptoms commensurate with a wild type infection are observed. The yield of purified virus from these plants is 13 mg out of 23 grams (0.57 mg/gram of plant material) following a standard procedure for CPMV purification (as mentioned above). Both viruses are analyzed on a denaturing 15 percent poly-acrylamide gel. The small coat protein shows no cleavage of these internal peptides as can sometimes be seen for peptides displayed in surface loops of CPMV.

Example 2

This Example demonstrates the expression and internal display of a hydrophobic peptide corresponding to a CTL-epitope (MAL 7) derived from the circumsporozoite protein of *Plasmodium berghei*. *P. berghei* is a unicellular protozoan causal agent of malaria in man. A peptide corresponding to an epitope from the circumsporozoite protein with the amino acid sequence SYIPSAEKI, can be expressed in the βBβC-loop of VP-S (giving rise to a chimeric virus particle designated Mal 4), and at two different positions in the C-terminus of VP-S (to generate respectively, Mal 5 and Mal 6). The same peptide can be expressed in the N-terminus of VP-S between a duplication of a tyrosine residue at position 11 in the protein (Tyr11; cf. Example 1). This construct is designated MAL 7. Initially following inoculation of cDNA encoding the modified CPMV MAL 7 onto the leaves of the host cowpea plants, the construct does not generate systemic symptoms. However after 21 days very clear local lesions are visible on the primary leaves of two out of five plants, indicating the establishment of an infection mediated by the inoculated CVP. Virus purified from these local lesions is transferred directly to two groups each of three young cowpea plants. Local lesions become visible within 5 days, and subsequent systemic infection follows within a week. This strongly improved viability in all likelihood indicates the selection of a virus from within the population carrying a de novo mutation in its genome. The RNA from virus purified 8 days post inoculation into the second two groups of cowpea plants is subjected to RT-PCR and sequencing of the resultant cDNA is carried out. The analysis reveals a point mutation, which is observed to have arisen independently in both sets of plants, and which is verified in each case by sequencing on both the plus and the minus strands of the cDNA produced in the RT-PCR reaction. However, this reversion is not present in 100 percent of the isolated viruses, since at this position a mixture of two nucleotides is observed in the automated sequencer chromatographs from each isolate. However, remarkably, in each case an adenosine is changed into a guanosine in the nucleotide sequence, causing a Glu to Gly mutation in the inserted peptide at the amino acid level. When the top leaves of the plants are analyzed 3 weeks after inoculation, a mixture of viral genomes is still observed, but the mutated genome is present in apparently greater numbers than the original sequence as judged by examination of the chromatographs. This indicates that the mutated VP-L has a competitive advantage over the un-mutated chimeric particle in its capacity to mount and progress a systemic spread of the virus within its host. Due to the mutated sequence of the peptide this construct cannot be used for an immunological analysis of the epitope concerned. However, it exemplifies two elements of the internalization of peptides system. First, the utility of a duplication of the tyrosine residue in the native sequence of the CPMV genome between which insertions of foreign peptides is demonstrated. This is required in some instances to maintain the putative binding site for the viral polyprotein protease. Second, the ability to select in vivo for altered chimeric virus particles whose characteristics render them amenable to infection and systemic spread within a cowpea plant is demonstrated. In this particular instance, the alteration in the recombinant viral genome directly affects the inserted foreign peptide itself. Mutations affecting peptides displayed externally on CPMV can be seen in instances where selection pressure in planta arises because the peptide possesses charge characteristics which imbalance the overall capsid protein shell's pI (see Definitions). The result described here is not anticipated because the rationale behind internalizing peptides is that surface charge inherent in the peptide in question should not represent a constraint once the peptide is deployed inside the virion. The following example identifies a completely unanticipated consequence of internalizing peptides within CPMV chimeric particles.

Example 3

This example demonstrates the in vivo generation and subsequent isolation of de novo mutations in chimeric virus genomes which confer selective advantage over the cognate wild type chimeric virus genome in the progression of infection and systemic spread of CVPs internally expressing MAL 7 peptides. The resultant mutant chimaera described in Example 2 (above) is, surprisingly, viable with regard to the recombinant virus's capacity to mount and progress a "natural" infection cycle, including systemic spread within the host plant. However, in an attempt to eliminate any structural constraints which, through selection pressure, might result in the mutation reported in MAL7 above, the insertion site is modified. Inspection of the crystal structure temperature factor shows that Val10 is in a relatively rigid conformation, whereas residue Asp9 is very flexible. This suggests that it should be possible to duplicate Val10Tyr11 so as simultaneously to preserve the protease binding site and to shift potentially destabilizing charged residues within the MAL7 peptide to a more C-terminal position in the VP-S N-terminus with respect to the original Val10Tyr11. The resultant chimaera is designated MAL8.

The MAL8 construct is used to infect host cowpea plants in a separate study. The profile of the initial infection is as seen for MAL 7 in Example 2. In detail, one plant out of five inoculated with cDNA encoding MAL 8 produces one local lesion after 21 days, indicating a limited infection with no apparent systemic spread of the virus. Virus purified from the local lesion is used to inoculate fresh cowpea plants. Symptoms of systemic spread of the chimeric virus particle within the plant are detectable after 5 days. This is indicative of improved infectivity most likely the consequence of a mutation in the viral genome. The genomes of virus isolated from the second round infection with MAL 8 are rendered into cDNA using RT-PCR and the gene encoding VP-S is sequenced along both strands. A de novo mutation is confirmed at nucleotide position 2931, altering a thymidine to a cytosine residue, thereby generating an amino acid change of phenylalanine at position 191 to a serine. This non-conservative change occurs at a point in the small coat protein, VP-S, which is situated at the interface between neighboring VP-S proteins in the virion. This mutation is apparently permissive for viable in vivo assembly and systemic spread of a chimeric CPMV particle in which a peptide is internally expressed. These data indicate that different de novo mutations permissive for the assembly in planta of CVPs capable of expressing internally a foreign peptide and capable of mounting the infection of and systemic spread within a cowpea host plant can be selected using CVPs expressing the same peptide internally. This further demonstrates that the location of the mutation within the virus particle and which is presumably driven by the structural constraints generated by the inserted peptide depend to some extent upon the precise insertion site used and not merely on the peptide itself.

Example 4

This Example demonstrates an in vivo procedure for the selection and isolation of de novo mutations in chimeric virus genomes which confer selective advantage over the cognate wild type chimeric virus genome in the progression of infection and systemic spread of CVPs internally expressing peptides. In order to rule out the possibility that the phenomenon described in Examples 2 and 3 is restricted to CVPs internally expressing malaria peptides, a procedure is followed to select for chimeric virus particles internally expressing peptides in which putative second site mutations occur. Mutations permissive for improved viability (meaning assembly into recombinant virions in planta), infectivity, systemic spread or productivity can be selected as described below. For the purposes of demonstration of the procedure, the enrichment and selection method is described with reference to a peptide, APGNYPAL, defining a CTL epitope derived from the nucleoprotein of Sendai virus. Briefly, cDNA is engineered to encode a chimeric virus particle in which the peptide (APGNYPAL, SEQ ID NO: 10) is inserted in between tyrosine residues at respectively, position 11 amino terminal and at position 20 carboxy-terminal to the peptide once inserted in VP-S of CPMV. The tyrosine at position 20 represents a duplication of the tyrosine at position 11 in the native VP-S and is used to maintain the putative polyprotein protease binding site (as discussed earlier). The resultant construct is designated pSEN1.

Upon inoculation of host cowpea plants with SEN1 symptoms of viral infection are slow to appear. After 18 days systemic infection is visible on only one out of five plants inoculated. The symptoms on the other four plants are restricted to local lesions on the inoculated leaves. Virus particles are isolated from all four plants in which infection is constrained to local lesions in the leaves, with viruses being isolated from a single lesion. The viral genomic RNA as isolated ex planta is reverse transcribed by RT-PCR. Subsequent sequencing on both strands of the cDNA so-produced indicates that the genomes of the viruses isolated from all four of the plants contain unaltered sequences. After a further 7 days (at day 25 post-infection) systemic spread is observed in 3 out of 5 plants inoculated. Virus is purified from systemically-infected leaves and the genomic RNA reverse transcribed. Sequence analysis of the resultant cDNA reveals a de novo mutation at nucleotide 3199 changing a guanosine residue for the wild type thymidine. Consequently, a leucine residue is incorporated at position 180 of the small coat protein (VP-S) in place of phenylalanine. This mutated genomic sequence correlates with successful infection of cowpea plants by chimeric CVP expressing internally a peptide derived from Sendai virus. This exemplifies the broad utility of the plant virus-host interaction as a dynamic means of enriching and selecting for novel CPMV genomes encoding chimeric virus particles capable of accommodating foreign peptides expressed inside the capsid. Taken together with Examples 2 and 3, this example demonstrates that the in vivo selection process can work on and be applied to CVPs expressing internally many different peptides and that mutations permissive for better infectivity and systemic spread of CVPs can occur at many different sites within the small coat protein of CPMV.

Example 5

This example demonstrates the expression internally of a CTL epitope derived from lymphocytic choriomeningitis virus (LCMV). The examples outlined above demonstrate that peptides with physico-chemical properties not conducive to expression externally on CVPs can be expressed internally. However, it is likely that there is a size constraint on the peptides which can be inserted to be expressed internally in the virion of CPMV. Thus foreign peptides amenable to internal expression are unlikely to be greater than 20 residues in length (although it is not impossible that empirical experimentation may identify peptides of greater length which are capable of being deployed internally). One class of peptides which fall within this size range are so-called cytotoxic T cell lymphocyte (CTL) epitopes. Importantly, CTL epitopes, in addition to being typically 6–9 residues in length, are conformation-independent. Indeed, there is strong evidence that CTL epitopes function as linear epitopes. Therefore such epitopes should be highly amenable to insertion internally in CVPs. One such epitope (RPQASGVYMGNLTAQ; SEQ ID NO: 6) is found on lymphocytic choriomeningitis virus. When displayed externally on CVPs this sequence poses problems due to its high positive charge. Therefore, three extra amino acids (glutamic acid, glycine and alanine) are added to its N-terminus in an effort to generate a peptide with a more neutral surface charge when it is expressed externally on a CVP. The symptoms produced upon infection of a host cowpea plant by this particular construct are variable and unpredictable since the chimeric virus produced is intrinsically unstable. In addition, there is severe cleavage of the externally presented epitope, and no T-cell response specific for the chimeric virus particles can be measured in mice. In order to confirm that CTL epitopes constitute an important class of foreign peptides capable of expression internally in CVPS, DNA encoding this known CTL epitope of lymphocytic choriomeningitis virus (RPQASGVYMGNLTAQ; SEQ ID NO: 6) is inserted into the N-terminus of VP-S.

The same epitope (without the additional amino acids Glu, Gly and Ala), is inserted in the N-terminus of the VP-S, at a position between Tyr11 and a duplicated tyrosine residue immediately downstream of the foreign peptide in a construct known as LCMV2. DNA inoculation results in viral symptoms in 3 out of 5 inoculated plants. RT-PCR analysis followed by sequencing of the product cDNA verifies that the sequence of the chimeric construct is unaltered and corresponds with that inoculated into the plant. The yield of the virus is 25 mg from 29 grams of leaves. Analysis by electrophoresis on a denaturing 15 percent poly-acrylamide gel confirms that there is no cleavage of the LCMV peptide as is anticipated for a peptide which is internalized. Hence it is demonstrated that a peptide representative of a large and immunologically important class of epitopes, cytotoxic T lymphocyte (CTL) epitopes, can be expressed internally in a chimeric virus particle. Moreover, the same particular peptide further confirms that internalization of positively-charged peptides in CVPs represents a technical solution to the unpredictability of behaviour and potential instability of CVPs expressing externally peptides with such characteristics. Furthermore, this demonstrates that a peptide of 15 amino acid residues in length can be successfully accommodated inside a CVP without the requirement for second site mutations.

Example 6

This example demonstrates the immunological efficacy of CTL epitopes expressed internally in chimeric virus particles. The CVP construct described above, LCMV2, which expresses a CTL epitope of lymphocytic choriomeningitis virus on the inside of the particle, is used to immunize mice. On day 0 and day 14 100 µg are injected subcutaneously, with or without an adjuvant, QS-21. As a control, wild type CPMV are also inoculated into test animals with and without QS21. On day 42 the spleens are removed, and CTL assays are performed 8 days later (see Current Protocols in Immunology, Vol. 1, section 3.11.4 and ff). Cytotoxic T-cells purified from mice infected with LCMV2 in QS-21 promote lysis of up to 46 percent of the target cells (FIG. 2). No CTL response is seen to LCMV2 in the absence of adjuvant. In mice inoculated with wild type CPMV, no specific CTL response is observed with or without the adjuvant. Besides the CTL response, a very strong epitope-specific T-helper response is observed in cells purified from the spleens of mice injected with LCMV2. It is clear from the immunological performance of the LCMV2 construct that CVPs with epitopes deployed on the inside of the particles can induce both a CTL response to a specific peptide and a strong peptide-specific T-helper response. No CTL responses were observed, however, in mice immunized with MAL8, VSV1, or SEN1. This may have to do with difficulties in processing the epitope in the antigen presenting cells.

Example 7

This Example demonstrates the synthesis of amphidisplay chimeric virus particles (ADCVPs, which are single chimeric virus particles expressing simultaneously epitopes internally and externally on a single virion. The ability to express peptides inside stable CPVs taken together with the ability (separately) to express a large range of peptides externally on stable CVPs raises the possibility that in a single particle at least two peptides can be presented simultaneously; one internally, the other externally. In particular, the presence internally of a T helper cell epitope may enhance the immune response to other epitopes co-expressed externally on the same particles. To test this notion use is made of an epitope (GVSTAPDTRPAPGSTA; SEQ ID NO: 35) associated with a variant form of the polymorphic epithelial mucin protein found predominantly on cells of solid tumors. The immunological profile of this epitope in CVPs is well characterized. Combinations of peptides known to be reactive in animal models are inserted into selected sites by molecular genetic manipulation of the CPMV genome. To date, three external sites are established as viable insertion points in VP-S for the external display of peptides on CVPs: the βBβC loop, the βC'βC" loop, and the carboxyl terminus; while a fourth external insertion site on CVPs is represented by the βEαB loop of VP-L. To test the efficacy of combining epitopes internally with epitopes externally on a single CVP, combinations are made as outlined in Table 3 below.

TABLE 3

Amphidisplay constructs in which peptides are deployed simultaneously inside and externally on CVPs

| CVP Construct Name | Peptide in N-terminus of CVP | Peptide in βB–βC loop of VP-S |
|---|---|---|
| MUC39 | 2F10 8-mer | MUC14 peptide |
| MUC40 | 2F10 15-mer | MUC14 peptide |
| HCG16 | 2F10 8-mer | HCG3 peptide |
| HCG17 | 2F10 15-mer | HCG3 peptide |

| CVP Construct Name | Peptide in N-terminus of CVP | Peptide in βB'βC" loop of VP-S |
|---|---|---|
| MUC47 | 2F10 8-mer | MUC peptide |
| MUC48 | 2F10 15-mer | MUC peptide |

TABLE 3-continued

Amphidisplay constructs in which peptides are deployed simultaneously inside and externally on CVPs

| CVP Construct Name | Peptide in N-terminus of CVP | Peptide in C-terminus VP-S |
|---|---|---|
| MUC41 | 2F10 8-mer | MUC8 peptide |
| MUC42 | 2F10 15-mer | MUC8 peptide |

The following constructs induce good symptoms (see earlier): MUC39, HCG16, MUC41, MUC42, and MUC47. These results indicate that insertions in the βBβC loop or the βC'βC" loop of VP-S can be combined most effectively with small (8 amino acid) insertions in the N-terminus of VP-S within the range of insertion sizes demonstrated above for this internal CVP site. However, insertions in the C-terminus of VP-S are apparently not as sensitive to the size of insertions in the N-terminus within the established range of insertion sizes.

Example 8

This Example demonstrates the immunological efficacy of amphidisplay chimeric virus particles (ADCVPs) in eliciting specific T-helper responses. The stimulating effect of a T-cell helper epitope in the N-terminus on the immune response to a B cell epitope inserted elsewhere is investigated by the immunological comparison of a CVP expressing a T helper cell epitope externally, with two different amphidisplay particles expressing the same T helper cell epitope internally in conjunction with different B cell epitopes. HBV15 is a CVP expressing an octamer derived from the 2F10 peptide in an internal site (see Example 1 above); MUC39 expresses the same octamer internally along with a peptide derived from the human variant mucin associated with solid tumors, MUC1p (MUC14) expressed externally in the βBβC loop; and MUC42 expresses simultaneously the same 2F10 mimotope internally and a MUC1p-derived peptide (MUCL) externally in the C terminus of VP-S (see preceding Example 7).

Three groups each of 5 mice are immunized with HBV15, MUC39 or MUC42 in the presence of QS-21 on days 0 and 21. Sera are collected on days 21, 28 and 42 and examined for both 2F10 and MUCI-specific antibodies by ELISA. The mean titres of antibodies specific for the mucin peptide are summarized in Table 4.

TABLE 4

MUC1p peptide-specific titres to various CVP constructs

| CVP Construct Name | Titer Day 21 | Titer Day 28 | Titer Day 42 |
|---|---|---|---|
| MUC14 | 51,200 | 14,703 | 104,840 |
| MUC39 | 86,107 | 52,730 | 204,800 |
| MUC42 | Not detectable | 696 | 235 |

At each time-point, mice immunized with MUC39 generate higher anti-MUC antibody titres (approximately one dilution higher) than mice immunized with MUC 14, suggesting that there may be a stimulating effect of the T-helper epitope on the anti-MUC B cell response. Of mice immunized with CPMV-MUC42, one out of five produce MUC1pspecific antibody: whereas when 2F10 is not co-expressed with a T helper cell epitope no mice produce MUC1 specific antibody. This reaction is at a modest level on day 28, and the titre declines by day 42. Thus the presence of the 2F10 a T helper cell epitope, can enhance the response to a B cell epitope exemplified by the Muc1p peptide.

When the 2F10-specific T cell responses are examined (Table 5), spleen cells from mice immunized with MUC39 proliferate in response to the 2F10 peptide. Consistent with the relatively low levels of Muc1p peptide-specific antibodies elicited by the MUC42 construct (Table 5), there is no apparent stimulation of proliferation of specific cells by the 2F110 peptide in this assay.

TABLE 5

T-cell proliferation stimulation indices

| CVP Construct name | No Stimulation | Stimulation with wt CPMV | Stimulation with 2F10 peptide |
| --- | --- | --- | --- |
| MUC39 | 1 | 13 | 14 |
| MUC42 | 1 | 28 | 1 |
| MUC14 | 1 | 3 | 1 |

These data indicate that the co-stimulation of an immune response with a CTL epitope can be used to trigger an enhanced response to a co-presented, but unrelated peptide.

Example 9

This Example demonstrates the expression and internalization of a powerful universal T-helper epitope through the selection of further de novo mutations at sites other than in the inserted peptide. A T-helper epitope derived from tetanus toxoid (VDDALINSTKIYSYFPSV; SEQ ID NO: 15) is known to have a strong immunostimulating effect in a wide range of organisms and with a correspondingly broad range of haplotypes. In order further to enhance the immunogenic properties of CPMV as an epitope presenting system, the tetanus toxoid can be incorporated into chimeric virus particles. In order to achieve this, the valine at position 10 (Val10) of VP-S is replaced by the epitope itself. Since the tetanus toxoid epitope begins and ends with a valine residue, there are by default ten "native" amino acids at the N-terminus of the mutated virus, which are likely to be sufficient to maintain the putative polyprotein protease binding site. This resultant construct is designated TT4. Following inoculation of cDNA directly onto cowpea plants (Daisgaard et al., supra), the TT4 construct shows symptoms of infection from day 14 onwards, in the form of local lesions on the inoculated leaves. Systemic infection of the host plants does not take place. Viruses purified from these local lesions are transferred directly onto young cowpea plants in a second round infection. Local lesions become visible within 5 days of infection, with systemic infection evident within a further 7 days. This improved viability in all likelihood indicates the selection within the population of viruses in which a de novo mutation has occurred in the viral genome. The RNA from virus purified 10 days after inoculation of the second group of cowpea plants is subjected to RT-PCR and sequencing of the resultant cDNA is carried out. The analysis reveals several single point mutations, which are verified by sequencing the cDNA on the opposite strand. Altogether six de novo mutations are observed in the various clones:

G2388A, which results in an Arg2102Lys mutation in the VP-L protein. (This mutation is observed arising independently in three separate clones);

A3188G, leading to a Met177Val mutation in the VP-S protein;

A3029G, leading to an Ile124Val mutation in the VP-S protein; and,

G2388A, resulting in an Ile2045Met mutation in the VP-S protein.

In order to test if these mutations are sufficient to render the TT4 construct infectious in a primary infection, 3 new constructs are generated using as the vector backbone novel chimeric virus particle genomes containing respectively, the G2388A (Arg2102Lys in VP-L), the A3188G (Met177Val in VP-S) and A3029G (Ile124Val) mutations. Plants inoculated with these new clones show local symptoms of infection 6 days post inoculation, and systemic symptoms within a further 4 days. This is a clear indication that single, second site mutations are sufficient to render the revised TT4 construct infectious.

This construct provides a demonstration of several features of the insertion of epitopes on the internal surface of CPMV. In the first instance, it demonstrates that T helper as well as CTL epitopes can be presented as internally deployed peptides in CVPS. Furthermore, it is clear that Tyr11 does not have to be duplicated in order to generate CVPs capable of mounting a viable infection in plants. The presence of 10 naturally occurring amino acids at the N-terminus of CPMV is sufficient for viability and infectivity. It is also clear that there are several different second site mutations that can greatly enhance the viability of a construct with an epitope inserted in the N-terminus of the VP-S of CPMV, and that these mutations can occur either in VP-S itself or in VP-L (the large coat protein). The fact that particular mutations are found independently in separate clones emphasizes that certain second sitemutations are more readily selected than others. This represents a means to identify mutational hotspots in the viral vector of utility in creating novel chimeric virus particle cloning vehicles capable of generating novel CVPs to display a broad range of foreign peptides.

Example 10

This Example demonstrates the expression and internalization of a powerful universal T-helper epitope derived from tetanus toxoid in combination with a B-cell epitope inserted in a loop of VP-L on the outside CPMV. Since the tetanus toxoid is a universal T-helper epitope, it is worth investigating the possibility of combining the display of this epitope on the inside of CPMV, as described in Example 9, such that it is co-expressed in a single particle with epitopes presented on the outer surface of a CVP. To this end a construct is made in which two peptides derived from *Pseudomonas aeruginosa* are inserted in tandem in the βEαB loop of the B-domain of the VP-L (peptides 9 and 10 of outer membrane protein, TDAYNQKLSERRAGADNA-TAEGRAINRRVEAE; SEQ ID NO: 36; Brennan et al., supra), while the tetanus toxoid epitope is inserted in the N-terminus of the VP-S. This construct is designated pPAE14. Following inoculation of cDNA directly onto cowpea plants, the PAE14 construct shows symptoms of infection (local lesions on inoculated leaves) from day 14 onwards. However, systemic infection of the host plants does not follow. Virus purified from these local lesions is transferred directly onto young cowpea plants in order to initiate a secondary infection. Local lesions become visible within 5 days, and subsequent systemic infection follows within a week. This indicates the selection of a novel virus whose genome has accrued a de novo mutation. The RNA from viruses purified 10 days post inoculation of the second group of cowpea plants is subjected to RT-PCR and sequencing of the resultant cDNA is carried out. The analysis reveals several single point mutations in the population which are confirmed by sequencing the cDNA of the opposite strand. Observed mutations in the various clones are:

A3029G, which leads to the mutation Ile124Val in the VP-S. (Cf. Example 9 in which a different mutation occurs at this same position); and T3189C, resulting in the mutation Met177Thr. (As above, a different mutation at this same position is reported in Example 9).

This example indicates that it is possible to express simultaneously an epitope on the inside of a chimeric plant virus such as CPMV, in combination with an epitope in VP-L so that it is presented externally. The second site mutations that are observed indicate that similar mutations can be found for different constructs (for example, A3029G in Example 9 and herein) and that different mutations so-selected can occur at a single amino acid position leading to a CVP with greatly enhanced infectivity.

Example 11

This Example demonstrates the expression and internalization of a powerful universal T-helper epitope derived from tetanus toxoid in combination with a B-cell epitope presented on the outside CPMV, inserted in a loop of VP-S. Since it is possible to combine the expression a universal T-helper epitope of on the inner surface of CPMV with an epitope on the outer surface of the virus by making use of the βEαB loop of the B-domain of the VP-L (Example 10), it is worth attempting to combine the expression of the tetanus toxoid epitope with the expression of epitopes in the βBβC loop of VP-S. A similar approach with the 2F10 mimotope of hepatitis B virus is described in Example 7.

Thus a construct is made in which the tetanus toxoid epitope is inserted in the N-terminus of VP-S, as described in Example 9, while a mucin-peptide (GVTSAPDTRPAPG-STA; SEQ ID NO: 37) is inserted in the βBβC-loop of VP-S, in between Ala22Pro23 essentially as described in Daisgaard et al., supra. This construct is designated pMUC51. Following inoculation of cDNA onto cowpea plants MUC51 does not show any symptoms of infection, even after 21 days. For this reason, a cDNA construct is made, identical to pMUC51 except that one second site mutation as reported in Example 9 (A3188G: Met177Val) is encoded in the chimeric virus vector. This novel construct is designated pMUC53. Following inoculation of cDNA onto cowpea plants the MUC53 construct does not show symptoms of infection until day 14. Systemic infection of the host plants does not occur. Viruses purified from these local lesions are transferred directly onto young cowpea plants to prime a second infection cycle. Local lesions become visible within 5 days, and subsequent systemic infection follows rapidly within 7 days. This likely indicates the selection of a further mutation in the virus genome. Viruses are purified from the plants 10 days post inoculation and the genomic RNA is rendered into cDNA by RT-PCR. Sequence analysis of both complementary strands confirms the occurrence of further de novo mutations:

G2357A, which leads to Ala492Thr in the VP-L; and

G2898A, causing Gly80Asp in the VP-S.

These experiments show several useful features of the internalization of epitopes. It is clear that it is possible to combine the insertion of epitopes in the βBβC-loop of the VP-S with epitopes in the N-terminus of the VP-S, even if the latter epitope is 18 amino acids residues in length. Furthermore it shows that in some cases second site mutations alone are not sufficient to generate an infectious construct, but that third site mutations need be selected to provide chimeric virus particles capable of mounting an infection. A method to select such higher order mutations as well as second site mutations is disclosed in Example 12 below.

Example 12

The following Example presents a protocol for the selection of novel chimeric virus particle genomes capable of the internalization and/or amphidisplay of peptides. Consideration of the foregoing examples informs a rationale for the selection in vivo of novel plant virus particles capable of accommodating internally peptides refractive to internalization or amphidisplay using wild type CVPs as vectors. Thus the following protocol and variants thereof can be used to select for novel CVP vectors.

1. A sequence encoding a peptide is cloned into an infectious cDNA molecule encoding CPMV-RNA (for example, pCP7 or pCP26), by the ligation of two or more hybridized oligonucleotides or a DNA fragment from an extraneous source. Use can be made of restriction sites that are adjacent to the sequence encoding the N-terminus of VP-S (for example, the unique Nhe1 and Eco01091 sites). The exact location in which the peptide is inserted is preferably between Val10 and Tyr11, between a duplication of Val10Tyr11, or between a duplication of Tyr11. It is also possible to use a cDNA clone in which peptide has already been inserted (for example, the βBβC loop of VP-S), so that several epitopes can be encoded and presented simultaneously on one particle.

2. In the case of cowpea mosaic virus, cowpea plants of approximately 10–14 days old (or at any other time during plant growth and before the onset of flowering*) are inoculated with the clone as constructed in step 1, in combination with a cDNA clone encoding CPMV-RNA1. (Any other susceptible host for CPMV may be infected at a suitable time before the onset of flowering*). [*Viruses are capable of mounting a systemic infection in the appropriate host plant until the growth phase has stopped and in the case of flowering plants, the onset of flowering occurs.]

3. Plants are monitored closely for the appearance of symptoms of infection. For a good replicating particle, local lesions on the inoculated leaves can be expected after 4–6 days, although they are not always clear. Systemic symptoms can be expected after 10–14 days post infection. If there are clear signs of systemic infection, the plants are harvested 3–4 weeks post infection, and the virus is purified (step 5). If it takes 14 days or longer before the first local lesions appear, and there are no or very few systemic symptoms until up to 3 weeks post infection, it is likely that spontaneous mutations have occurred in planta. In this case, the virus needs be transferred to fresh plants, as in step 4. If there are no detectable symptoms at all, additional mutations may be required (see steps 7 and 8).

4. If the only symptoms are local lesions rather than systemic lesions, which become apparent 2 weeks or more post infection (and before the onset of flowering or the cessation of the growth phase of the plant), these are cut out of the leaves and individually transferred to a test tube. Some water or any buffer suitable for the storage of virus particles is added to each test tube, and the leaf fragments are crushed. The resulting suspension is used to inoculate fresh young cowpea plants (or other appropriate host plant) as described in step 2. This will lead to local lesions approximately 5 days post infection and systemic symptoms 3–6 days later.

The leaves are harvested. Virus can be purified from leaves, for example, by chloroform/butanol extraction followed by PEG-precipitation (van Kammen & de Jaeger Cowpea mosaic virus, In: CMI/AAB Description of Plant Viruses 197, Commonwealth Agricultural Bureaux [1978]). Samples are purified from each individual plant for sequence analysis (Brennan et al., supra).

6. The viral particles are used in a standard RT-reaction with a primer that is capable of specific hybridization to and priming of reverse transcription of either the VP-S gene or the VP-L gene. The RT-product is amplified by means of PCR using primers that amplify either the VP-S gene or the VP-L gene, or both. The PCR products are sequenced, such that the sequence of the VP-S, the VP-L or both can be determined on both strands. If there are no mutations in the inserted epitopes, the construct can be used for, inter alia, immunological analysis.

7. If second site mutations are identified, these can be introduced into novel derivatives of the cDNA clones described in step 1, either by site directed mutagenesis, or by cutting and pasting fragments from the cDNA of step 6 into the infectious clone.

8. If in step 4 there are no symptoms at all, a known second site mutation identified in a different construct, or any other mutation that may generate an infectious clone can be introduced in the cDNA clone made in step 1 and modified as in step 7. With the new construct repeat the whole infection procedure, following steps 2–5. If there are good symptoms in step 4, the introduced mutation may be sufficient for infection and replication of CVPs in planta. If there are only local lesions, it is likely that third site mutations have taken place. This can be investigated or confirmed by following steps 5 and 6.

9. A bank can be made of virus vectors with various second site or third site (or further site) mutations, into which an epitope can be ligated as described in step 1 above. In this case it is important to proceed with the transfer of a local lesion in step 4, to make sure that the systemically infected plants contain one single clone of the virus.

Example 13

This Example demonstrates the application of a de novo second site mutation to enhance the infectivity and replication of a virus vector expressing a foreign peptide other than the peptide whose internal expression generated the pressure for the selection of the mutation in vivo. A peptide derived from the nucleocapsid protein of Sendai Virus (with the amino acid sequence, HGEFAPGNYPALWYSA; SEQ ID NO: 11) is inserted in the N-terminus of the VP-S of CPMV, at a site between duplicated tyrosine residues (that is, Tyr11 amino-terminal to the inserted peptide and a second tyrosine residue immediately carboxyl-terminal to the inserted sequence). This construct is designated pSEN2. Following inoculation of cDNA on cowpea plants, the SEN2 does not show any symptoms after 21 days. For this reason a construct is made which is similar to pSEN2, but differs in that the chimeric virus vector contains a second site mutation, Phe91Ser, selected in a construct expressing a malaria epitope (MAL8; see Example 3). This construct is designated pSEN3. Following inoculation of cDNA on cowpea plants the SEN3 construct shows symptoms of infection on the inoculated leaves from as early as day 6, and systemic symptoms appear 4 days later on 4 out of 5 inoculated plants. The plants are harvested 21 days post infection. Virus is purified from the inoculated leaves, and a yield of 50 mg virus from 47 g of leaves is observed. The RNA from virus purified 21 days post inoculation is subjected to RT-PCR and sequencing of the resultant cDNA on both strands is carried out. Analysis reveals that the sequence is unchanged from the sequence of the pSEN3 construct used to inoculate the plants.

This clearly demonstrates that it is possible to apply a particular second site mutation, selected in a construct expressing one peptide internally, to facilitate the expression internally of another unrelated peptide inserted at essentially the same position. This indicates that second site mutations have broad utility in the expression internally of peptides and in principle in the construction of further amphidisplay particles according to Examples 7 and 8. Thus it is possible following the means outlined in Examples 12 and 13 herein to construct a bank of vectors which can be tested for the expression of peptides on the inside of the virus without undue experimentation.

Example 14

This Example demonstrates the expression of a T-cell epitope on the inside of a plant virus particle to obviate exposure of that epitope to elements of the humoral immune response (for example, circulating antibodies) and immunomodulation by route of immunogen or antigen presentation. The aim of many peptide based vaccines is the induction of a cellular rather than a humoral (antibody) response to the epitope being presented. In particular, therapeutic intervention in cancer is increasingly recognised as being all the more effective if a cellular immune response can be stimulated. However, since the presented epitope of interest can be recognised by antibodies circulating in the serum as well, there is always the chance that the immunogen introduced to stimulate a desired immune response may induce a humoral rather than a cellular response to the presented peptide. Moreover, the adventitious presence of circulating antibodies capable of binding the introduced immunogenic or antigenic composition may preclude the appropriate and effective stimulation of a desired immune response by clearing the complex. Indeed, this is potentially a problem with any peptide-presenting system in which peptides are displayed on the exterior of a macromolecular carrier such as keyhole limpet haemocyanin (KLH). On the other hand, expressing a peptide such as an epitope inside a particle, for example, in a plant chimeric virus, protects that peptide from the binding of antibodies. Not only does this impede an unwanted humoral response to the epitope, it also assists in allowing the peptide to survive clearance and proteolysis until it has been presented to and processed by antigen presenting cells (APCS) of the immune system. For these reasons, the internalization of epitopes in CPMV or other plant viruses has applicability for the expression of epitopes that may crossreact with circulating antibodies, and hence can be used to direct the type of immune response from a humoral to a cellular response. This holds for the expression of peptide mimotopes as well.

For immunotherapeutic applications with peptides the induction of particularly cytotoxic Tcells is required. For this to happen, epitopes capable of eliciting a cytotoxic T cell response must be delivered to and presented by cells so that the peptide epitope is processed and presented on MHC molecules. Presentation by this route obviates a direct antibody response and instead elicits the stimulation of specific cytotoxic T lymphocyte populations. Such lymphocytes subsequently target cells displaying the peptide in question directly, leading to cell lysis or clearance of the target cells or antigens following opsonisation.

It is known that a peptide derived from a protein, mucin, found in large amounts on the surface of breast (and other) human cancer cells is able to induce CTL responses in mice when coupled to a carrier. The mucin polypeptide as found on cancer cells differs from the ubiquitous form of the protein found on the surface of many noncancer cells in that it is differently post-translationally modified. In attempts to immunize test animals with a mucin peptide-containing vaccine. Muc1p cross-reactive antibodies in mice are found to switch the immune response elicited from a cellular to a humoral one. When the same immunogen is used to vaccinate humans, an antibody response rather than a cellular response follows, since the antigenic peptide cross-reacts with antibodies against the Gal alpha(1,3)Gal epitope, normally present on determinants of some blood groupings in humans, but not found in mice.

One technical solution is to express the same peptide as an insertion in the N-terminus of the VP-S of CPMV, in between a duplication of Tyr11. When these particles are used to immunize humans, antibodies cannot bind to the inserted epitope directly. A cellular response to the epitope take place in preference through the uptake and presentation of the Muc1p peptide on antigen presenting cells (APCs). The stimulation of CTL sub-populations specific for the Muc1p peptide epitope results in lysis or clearance of target cells bearing essentially the same epitope in their cell membranes.

Example 15

This Example demonstrates the production of a CVP containing a CTL epitope from measles virus. A CTL-epitope from measles virus (LDRLVRLIG; SEQ ID NO: 13), which is positively charged, was inserted in the N-terminus of VP-S, in between a duplication of Y11. This construct is pMV14. Plants inoculated with this construct did not show any symptoms. The same epitope was inserted in between a duplication of V10Y11 (=pMV15), and now symptoms were observed on two out of five inoculated plants. When purified virus was transferred to young cowpea plants very good symptoms were observed. Both coat protein genes were sequenced completely and found to be correct.

Example 16

This Example demonstrates the production of a CVP containing a CTL epitope from vesicular stomatitis virus. A CTL-epitope of Vesicular stomatitis virus (RGYWQGL; SEQ ID NO: 12) has been successfully expressed on TY-particles, and these particles induced very good CTL responses in mice (Layton et al., Immunology 87: 171–178 [1996]). This same epitope was inserted in between duplicated Y11 in VP-S of CPMV. This construct is pVSVI. Good symptoms were seen on 4 out of 5 plants inoculated with this construct. The virus gave good yields (0.79 mg/gram leaves).

Example 17

This Example demonstrates the construction of vectors containing oligo-alanine flanking a CTL epitope. It is known that for the proper processing of CTL epitopes by the antigen presenting cells, the residues flanking the epitope are crucial. Very little is known however, about which residues are optimal in conjunction with certain epitopes. It has been observed that inserting short stretches of alanines on either site of the epitope can be helpful in improving the response to a CTL epitope inserted in a protein carrier (Del Val et al., Cell 66:1145–1153 [1991]).

A vector has been made with five alanines in between a duplication of V10Y11, while there is a unique NotI site in this insert (pCP35). The vector by itself was infectious an cowpea plants, albeit that the viral symptoms were delayed with respect to WT virus. Inserting epitopes in this oligo-A stretch can be useful to study the optimization of CTL-epitope processing in case epitopes give only weak immune responses. A malaria epitope was inserted in the NotI site to make pMAL11. This construct gave good symptoms on plants.

Since no CTL response was observed to the measles virus epitope of pMV15 in mice (see above), an additional construct was made in which this epitope was flanked by several alanines on either side. This construct, pMV16, was not infectious on cowpea plants. In analogy to pSEN3 (see above), a second site mutation from an unrelated construct was applied to pMV16 (M177V, derived from pTT4). This construct, which was called pMV17 did not give any symptoms on plants.

The following useful plant viral vectors are on deposit at the American Type Culture Collection (ATCC), Rockville, Md., USA, under the terms of the Budapest Treaty on the International Recognition of the Deposit of Microorganisms for the Purposes of Patent Procedure and Regulations thereunder: pTB2 (ATCC No. 75280) and pTBU5 (ATCC 75281). The construction details for these plasmids are set forth in U.S. Pat. No. 5,589,367 hereby incorporated by reference.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A compound comprising a chimeric viral particle comprising at least one exogenous peptide inserted in VP-S of cowpea mosaic virus between a tyrosine residue at position 11 and a duplicated tyrosine residue at position 12.

2. A chimeric viral particle according to claim 1 which is capable of assembly in a host cell or tissue.

3. A chimeric virus particle according to claim 1, wherein the exogenous peptide comprises a cytotoxic T lymphocyte epitope.

4. A chimeric virus particle according to claim 3 wherein the cytotoxic T lymphocyte epitope is derived from the cicumsporozoite protein of *Plasmodium berghei*.

5. A chimeric virus particle according to claim 4, wherein the cytotoxic T lymphocyte epitope has the sequence of SEQ ID NO: 7.

6. A chimeric virus particle according to claim 3, wherein the cytotoxic T lymphocyte epitope is derived from the lymphocytic choriomeningitis virus.

7. A chimeric virus particle according to claim 6, wherein the cytotoxic T lymphocyte epitope has the sequence of SEQ ID NO: 6.

8. A chimeric virus particle according to claim 6 wherein the cytotoxic T lymphocyte epitope is derived from the nucleocapsid protein of Sendai virus.

9. A chimeric virus particle according to claim 1, wherein the exogenous epitope is a helper T lymphocyte epitope.

10. A chimeric virus particle according to claim 1, wherein the exogenous peptide comprises a T lymphocyte epitope.

* * * * *